(12) United States Patent
Carcieri et al.

(10) Patent No.: US 12,144,995 B2
(45) Date of Patent: *Nov. 19, 2024

(54) POINT-AND-CLICK PROGRAMMING FOR DEEP BRAIN STIMULATION USING REAL-TIME MONOPOLAR REVIEW TRENDLINES

(71) Applicant: Boston Scientific Neuromodulation Corporation, Valencia, CA (US)

(72) Inventors: Stephen Carcieri, Los Angeles, CA (US); Dean Chen, Irvine, CA (US); Michael A. Moffitt, Solon, OH (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/423,134

(22) Filed: Jan. 25, 2024

(65) Prior Publication Data

US 2024/0157157 A1  May 16, 2024

Related U.S. Application Data

(60) Continuation of application No. 18/118,660, filed on Mar. 7, 2023, now Pat. No. 11,938,328, which is a
(Continued)

(51) Int. Cl.
*A61N 1/372* (2006.01)
*A61N 1/05* (2006.01)
(Continued)

(52) U.S. Cl.
CPC ....... *A61N 1/37247* (2013.01); *A61N 1/0534* (2013.01); *A61N 1/3605* (2013.01);
(Continued)

(58) Field of Classification Search
None
See application file for complete search history.

(56) References Cited

U.S. PATENT DOCUMENTS 3,999,555 A    12/1976  Person
4,144,889 A     3/1979  Tyers et al.
(Continued)

FOREIGN PATENT DOCUMENTS

EP    1048320    11/2000
EP    1166819     1/2002
(Continued)

OTHER PUBLICATIONS

U.S. Appl. No. 18/118,660, filed Mar. 7, 2023.
(Continued)

*Primary Examiner* — Mallika D Fairchild
(74) *Attorney, Agent, or Firm* — Branch Partners PLLC; Bruce E. Black

(57) ABSTRACT

A system and method for selecting leadwire stimulation parameters includes a processor iteratively performing, for each of a plurality of values for a particular stimulation parameter, each value corresponding to a respective current field: (a) shifting the current field longitudinally and/or rotationally to a respective plurality of locations about the leadwire; and (b) for each of the respective plurality of locations, obtaining clinical effect information regarding a respective stimulation of the patient tissue produced by the respective current field at the respective location; and displaying a graph plotting the clinical effect information against values for the particular stimulation parameter and locations about the leadwire, and/or based on the obtained clinical effect information, identifying an optimal combination of a selected value for the particular stimulation param-
(Continued)

eter and selected location about the leadwire at which to perform a stimulation using the selected value.

20 Claims, 8 Drawing Sheets

Related U.S. Application Data continuation of application No. 17/170,677, filed on Feb. 8, 2021, now Pat. No. 11,633,608, which is a continuation of application No. 16/284,917, filed on Feb. 25, 2019, now Pat. No. 10,946,201, which is a continuation of application No. 15/991,807, filed on May 29, 2018, now Pat. No. 10,265,532, which is a continuation of application No. 15/729,383, filed on Oct. 10, 2017, now Pat. No. 10,016,610, which is a continuation of application No. 15/420,842, filed on Jan. 31, 2017, now Pat. No. 9,821,167, which is a division of application No. 15/012,698, filed on Feb. 1, 2016, now Pat. No. 9,561,380, which is a division of application No. 14/011,817, filed on Aug. 28, 2013, now Pat. No. 9,248,296.

(60) Provisional application No. 61/753,232, filed on Jan. 16, 2013, provisional application No. 61/699,115, filed on Sep. 10, 2012, provisional application No. 61/699,135, filed on Sep. 10, 2012, provisional application No. 61/693,866, filed on Aug. 28, 2012.

(51) Int. Cl.
 A61N 1/36 (2006.01)
 G16H 40/63 (2018.01)
 G16Z 99/00 (2019.01)

(52) U.S. Cl.
 CPC ......... *A61N 1/36185* (2013.01); *A61N 1/372* (2013.01); *G16H 40/63* (2018.01); *G16Z 99/00* (2019.02); *A61N 1/36082* (2013.01)

(56) References Cited

U.S. PATENT DOCUMENTS

| | | |
|---|---|---|
| 4,177,818 A | 12/1979 | De Pedro |
| 4,341,221 A | 7/1982 | Testerman |
| 4,378,797 A | 4/1983 | Osterholm |
| 4,445,500 A | 5/1984 | Osterholm |
| 4,735,208 A | 4/1988 | Wyler et al. |
| 4,765,341 A | 8/1988 | Mower et al. |
| 4,841,973 A | 6/1989 | Stecker |
| 5,067,495 A | 11/1991 | Brehm |
| 5,099,846 A | 3/1992 | Hardy |
| 5,222,494 A | 6/1993 | Baker, Jr. |
| 5,255,693 A | 10/1993 | Dutcher |
| 5,259,387 A | 11/1993 | dePinto |
| 5,304,206 A | 4/1994 | Baker, Jr. et al. |
| 5,344,438 A | 9/1994 | Testerman et al. |
| 5,361,763 A | 11/1994 | Kao et al. |
| 5,452,407 A | 9/1995 | Crook |
| 5,565,949 A | 10/1996 | Kasha, Jr. |
| 5,593,427 A | 1/1997 | Gliner et al. |
| 5,601,612 A | 2/1997 | Gliner et al. |
| 5,607,454 A | 3/1997 | Cameron et al. |
| 5,620,470 A | 4/1997 | Gliner et al. |
| 5,651,767 A | 7/1997 | Schulman |
| 5,711,316 A | 1/1998 | Elsberry et al. |
| 5,713,922 A | 2/1998 | King |
| 5,716,377 A | 2/1998 | Rise et al. |
| 5,724,985 A | 3/1998 | Snell et al. |
| 5,749,904 A | 5/1998 | Gliner et al. |
| 5,749,905 A | 5/1998 | Gliner et al. |
| 5,776,170 A | 7/1998 | MacDonald et al. |
| 5,782,762 A | 7/1998 | Vining |
| 5,843,148 A | 12/1998 | Gijsbers et al. |
| 5,859,922 A | 1/1999 | Hoffmann |
| 5,868,740 A | 2/1999 | LeVeen et al. |
| 5,897,583 A | 4/1999 | Meyer et al. |
| 5,910,804 A | 6/1999 | Fortenbery et al. |
| 5,925,070 A | 7/1999 | King et al. |
| 5,938,688 A | 8/1999 | Schiff |
| 5,938,690 A | 8/1999 | Law et al. |
| 5,978,713 A | 11/1999 | Prutchi et al. |
| 6,016,449 A | 1/2000 | Fischell et al. |
| 6,029,090 A | 2/2000 | Herbst |
| 6,029,091 A | 2/2000 | de la Rama et al. |
| 6,050,992 A | 4/2000 | Nichols |
| 6,058,331 A | 5/2000 | King |
| 6,066,163 A | 5/2000 | John |
| 6,083,162 A | 7/2000 | Vining |
| 6,094,598 A | 7/2000 | Elsberry et al. |
| 6,096,756 A | 8/2000 | Crain et al. |
| 6,106,460 A | 8/2000 | Panescu et al. |
| 6,109,269 A | 8/2000 | Rise et al. |
| 6,128,538 A | 10/2000 | Fischell et al. |
| 6,129,685 A | 10/2000 | Howard, III |
| 6,146,390 A | 11/2000 | Heilbrun et al. |
| 6,161,044 A | 12/2000 | Silverstone |
| 6,167,311 A | 12/2000 | Rezai |
| 6,181,969 B1 | 1/2001 | Gord |
| 6,192,266 B1 | 2/2001 | Dupree et al. |
| 6,205,361 B1 | 3/2001 | Kuzma |
| 6,208,881 B1 | 3/2001 | Champeau |
| 6,240,308 B1 | 5/2001 | Hardy et al. |
| 6,246,912 B1 | 6/2001 | Sluijter et al. |
| 6,253,109 B1 | 6/2001 | Gielen |
| 6,289,239 B1 | 9/2001 | Panescu et al. |
| 6,301,492 B1 | 10/2001 | Zonenshayn |
| 6,310,619 B1 | 10/2001 | Rice |
| 6,319,241 B1 | 11/2001 | King |
| 6,336,899 B1 | 1/2002 | Yamazaki |
| 6,343,226 B1 | 1/2002 | Sunde et al. |
| 6,351,675 B1 | 2/2002 | Tholen et al. |
| 6,353,762 B1 | 3/2002 | Baudino et al. |
| 6,366,813 B1 | 4/2002 | Dilorenzo |
| 6,368,331 B1 | 4/2002 | Front et al. |
| 6,389,311 B1 | 5/2002 | Whayne et al. |
| 6,393,325 B1 | 5/2002 | Mann et al. |
| 6,421,566 B1 | 7/2002 | Holsheimer |
| 6,435,878 B1 | 8/2002 | Reynolds et al. |
| 6,442,432 B2 | 8/2002 | Lee |
| 6,463,328 B1 | 10/2002 | John |
| 6,491,699 B1 | 12/2002 | Henderson et al. |
| 6,494,831 B1 | 12/2002 | Koritzinsky |
| 6,507,759 B1 | 1/2003 | Prutchi et al. |
| 6,510,347 B2 | 1/2003 | Borkan |
| 6,516,227 B1 | 2/2003 | Meadows et al. |
| 6,517,480 B1 | 2/2003 | Krass |
| 6,539,263 B1 | 3/2003 | Schiff |
| 6,560,490 B2 | 5/2003 | Grill et al. |
| 6,579,280 B1 | 6/2003 | Kovach et al. |
| 6,600,956 B2 | 7/2003 | Maschino et al. |
| 6,606,523 B1 | 8/2003 | Jenkins |
| 6,609,029 B1 | 8/2003 | Mann et al. |
| 6,609,031 B1 | 8/2003 | Law et al. |
| 6,609,032 B1 | 8/2003 | Woods et al. |
| 6,622,048 B1 | 9/2003 | Mann et al. |
| 6,631,297 B1 | 10/2003 | Mo |
| 6,654,642 B2 | 11/2003 | North et al. |
| 6,662,053 B2 | 12/2003 | Borkan |
| 6,675,046 B2 | 1/2004 | Holsheimer |
| 6,684,106 B2 | 1/2004 | Herbst |
| 6,687,392 B1 | 2/2004 | Touzawa et al. |
| 6,690,972 B2 | 2/2004 | Conley et al. |
| 6,690,974 B2 | 2/2004 | Archer et al. |
| 6,692,315 B1 | 2/2004 | Soumillion et al. |
| 6,694,162 B2 | 2/2004 | Hartlep |
| 6,694,163 B1 | 2/2004 | Vining |
| 6,708,096 B1 | 3/2004 | Frei et al. |
| 6,741,892 B1 | 5/2004 | Meadows et al. |
| 6,748,098 B1 | 6/2004 | Rosenfeld |
| 6,748,276 B1 | 6/2004 | Daignault, Jr. et al. |

(56) References Cited

U.S. PATENT DOCUMENTS

| | | |
|---|---|---|
| 6,778,846 B1 | 8/2004 | Martinez et al. |
| 6,788,969 B2 | 9/2004 | Dupree et al. |
| 6,795,737 B2 | 9/2004 | Gielen et al. |
| 6,827,681 B2 | 12/2004 | Tanner et al. |
| 6,830,544 B2 | 12/2004 | Tanner |
| 6,845,267 B2 | 1/2005 | Harrison et al. |
| 6,850,802 B2 | 2/2005 | Holsheimer |
| 6,895,280 B2 | 5/2005 | Meadows et al. |
| 6,909,913 B2 | 6/2005 | Vining |
| 6,937,891 B2 | 8/2005 | Leinders et al. |
| 6,937,903 B2 | 8/2005 | Schuler et al. |
| 6,944,497 B2 | 9/2005 | Stypulkowski |
| 6,944,501 B1 | 9/2005 | Pless |
| 6,950,707 B2 | 9/2005 | Whitehurst |
| 6,969,388 B2 | 11/2005 | Goldman et al. |
| 7,003,349 B1 | 2/2006 | Andersson et al. |
| 7,003,352 B1 | 2/2006 | Whitehurst |
| 7,008,370 B2 | 3/2006 | Tanner et al. |
| 7,008,413 B2 | 3/2006 | Kovach et al. |
| 7,035,690 B2 | 4/2006 | Goetz |
| 7,043,293 B1 | 5/2006 | Baura |
| 7,047,082 B1 | 5/2006 | Schrom et al. |
| 7,047,084 B2 | 5/2006 | Erickson et al. |
| 7,050,857 B2 | 5/2006 | Samuelsson et al. |
| 7,054,692 B1 | 5/2006 | Whitehurst et al. |
| 7,058,446 B2 | 6/2006 | Schuler et al. |
| 7,082,333 B1 | 7/2006 | Bauhahn et al. |
| 7,107,102 B2 | 9/2006 | Daignault et al. |
| 7,126,000 B2 | 10/2006 | Ogawa et al. |
| 7,127,297 B2 | 10/2006 | Law et al. |
| 7,136,518 B2 | 11/2006 | Griffin et al. |
| 7,136,695 B2 | 11/2006 | Pless et al. |
| 7,142,923 B2 | 11/2006 | North et al. |
| 7,146,219 B2 | 12/2006 | Sieracki et al. |
| 7,146,223 B1 | 12/2006 | King |
| 7,151,961 B1 | 12/2006 | Whitehurst |
| 7,155,279 B2 | 12/2006 | Whitehurst |
| 7,167,760 B2 | 1/2007 | Dawant et al. |
| 7,177,674 B2 | 2/2007 | Echauz et al. |
| 7,181,286 B2 | 2/2007 | Sieracki et al. |
| 7,184,837 B2 | 2/2007 | Goetz |
| 7,191,014 B2 | 3/2007 | Kobayashi et al. |
| 7,209,787 B2 | 4/2007 | Dilorenzo |
| 7,211,050 B1 | 5/2007 | Caplygin |
| 7,216,000 B2 | 5/2007 | Sieracki et al. |
| 7,217,276 B2 | 5/2007 | Henderson |
| 7,218,968 B2 | 5/2007 | Condie et al. |
| 7,228,179 B2 | 6/2007 | Campen et al. |
| 7,231,254 B2 | 6/2007 | DiLorenzo |
| 7,236,830 B2 | 6/2007 | Gliner |
| 7,239,910 B2 | 7/2007 | Tanner |
| 7,239,916 B2 | 7/2007 | Thompson et al. |
| 7,239,926 B2 | 7/2007 | Goetz |
| 7,242,984 B2 | 7/2007 | DiLorenzo |
| 7,244,150 B1 | 7/2007 | Brase et al. |
| 7,252,090 B2 | 8/2007 | Goetz |
| 7,254,445 B2 | 8/2007 | Law et al. |
| 7,254,446 B1 | 8/2007 | Erickson |
| 7,257,447 B2 | 8/2007 | Cates et al. |
| 7,266,412 B2 | 9/2007 | Stypulkowski |
| 7,294,107 B2 | 11/2007 | Simon et al. |
| 7,295,876 B1 | 11/2007 | Erickson |
| 7,299,096 B2 | 11/2007 | Balzer et al. |
| 7,308,302 B1 | 12/2007 | Schuler et al. |
| 7,313,430 B2 | 12/2007 | Urquhart |
| 7,324,851 B1 | 1/2008 | DiLorenzo |
| 7,346,382 B2 | 3/2008 | McIntyre et al. |
| 7,388,974 B2 | 6/2008 | Yanagita |
| 7,437,193 B2 | 10/2008 | Parramon et al. |
| 7,463,928 B2 | 12/2008 | Lee et al. |
| 7,499,048 B2 | 3/2009 | Sieracki et al. |
| 7,505,815 B2 | 3/2009 | Lee et al. |
| 7,548,786 B2 | 6/2009 | Lee et al. |
| 7,565,199 B2 | 7/2009 | Sheffield et al. |
| 7,603,177 B2 | 10/2009 | Sieracki et al. |
| 7,617,002 B2 | 11/2009 | Goetz |
| 7,623,918 B2 | 11/2009 | Goetz |
| 7,650,184 B2 | 1/2010 | Walter |
| 7,657,319 B2 | 2/2010 | Goetz et al. |
| 7,672,734 B2 | 3/2010 | Anderson et al. |
| 7,676,273 B2 | 3/2010 | Goetz et al. |
| 7,680,526 B2 | 3/2010 | McIntyre et al. |
| 7,734,340 B2 | 6/2010 | De Ridder |
| 7,761,165 B1 | 7/2010 | He et al. |
| 7,826,902 B2 | 11/2010 | Stone et al. |
| 7,848,802 B2 | 12/2010 | Goetz et al. |
| 7,860,548 B2 | 12/2010 | McIntyre et al. |
| 7,904,134 B2 | 3/2011 | McIntyre et al. |
| 7,945,105 B1 | 5/2011 | Jaenisch |
| 7,949,395 B2 | 5/2011 | Kuzma |
| 7,974,706 B2 | 7/2011 | Moffitt et al. |
| 8,019,439 B2 | 9/2011 | Kuzma et al. |
| 8,175,710 B2 | 5/2012 | He |
| 8,180,601 B2 | 5/2012 | Butson et al. |
| 8,195,300 B2 | 6/2012 | Gliner et al. |
| 8,224,450 B2 | 7/2012 | Brase |
| 8,257,684 B2 | 9/2012 | Covalin et al. |
| 8,262,714 B2 | 9/2012 | Hulvershorn et al. |
| 8,364,278 B2 | 1/2013 | Pianca et al. |
| 8,429,174 B2 | 4/2013 | Ramani et al. |
| 8,452,415 B2 | 5/2013 | Goetz et al. |
| 8,543,189 B2 | 9/2013 | Paitel et al. |
| 8,606,360 B2 | 12/2013 | Butson et al. |
| 8,620,452 B2 | 12/2013 | King et al. |
| 8,918,184 B1 | 12/2014 | Torgerson et al. |
| 2001/0031071 A1 | 10/2001 | Nichols et al. |
| 2002/0032375 A1 | 3/2002 | Bauch et al. |
| 2002/0062143 A1 | 5/2002 | Baudino et al. |
| 2002/0087201 A1 | 7/2002 | Firlik et al. |
| 2002/0099295 A1 | 7/2002 | Gil et al. |
| 2002/0115603 A1 | 8/2002 | Whitehouse |
| 2002/0116030 A1 | 8/2002 | Rezei |
| 2002/0123780 A1 | 9/2002 | Grill et al. |
| 2002/0128694 A1 | 9/2002 | Holsheimer |
| 2002/0151939 A1 | 10/2002 | Rezai |
| 2002/0183607 A1 | 12/2002 | Bauch et al. |
| 2002/0183740 A1 | 12/2002 | Edwards et al. |
| 2002/0183817 A1 | 12/2002 | Van Venrooij et al. |
| 2003/0097159 A1 | 5/2003 | Schiff et al. |
| 2003/0149450 A1 | 8/2003 | Mayberg |
| 2003/0171791 A1 | 9/2003 | KenKnight et al. |
| 2003/0212439 A1 | 11/2003 | Schuler et al. |
| 2004/0034394 A1 | 2/2004 | Woods et al. |
| 2004/0044279 A1 | 3/2004 | Lewin et al. |
| 2004/0044378 A1 | 3/2004 | Holsheimer |
| 2004/0044379 A1 | 3/2004 | Holsheimer |
| 2004/0054297 A1 | 3/2004 | Wingeier et al. |
| 2004/0059395 A1 | 3/2004 | North et al. |
| 2004/0106916 A1 | 6/2004 | Quaid et al. |
| 2004/0133248 A1 | 7/2004 | Frei et al. |
| 2004/0152957 A1 | 8/2004 | Stivoric et al. |
| 2004/0181262 A1 | 9/2004 | Bauhahn |
| 2004/0186532 A1 | 9/2004 | Tadlock |
| 2004/0199216 A1 | 10/2004 | Lee et al. |
| 2004/0267330 A1 | 12/2004 | Lee et al. |
| 2005/0021090 A1 | 1/2005 | Schuler et al. |
| 2005/0033380 A1 | 2/2005 | Tanner et al. |
| 2005/0049649 A1 | 3/2005 | Luders et al. |
| 2005/0060001 A1 | 3/2005 | Singhal et al. |
| 2005/0060009 A1 | 3/2005 | Goetz |
| 2005/0070781 A1 | 3/2005 | Dawant et al. |
| 2005/0075689 A1 | 4/2005 | Toy et al. |
| 2005/0085714 A1 | 4/2005 | Foley et al. |
| 2005/0165294 A1 | 7/2005 | Weiss |
| 2005/0171587 A1 | 8/2005 | Daglow et al. |
| 2005/0228250 A1 | 10/2005 | Bitter et al. |
| 2005/0251061 A1 | 11/2005 | Schuler et al. |
| 2005/0261061 A1 | 11/2005 | Nguyen et al. |
| 2005/0261601 A1 | 11/2005 | Schuler et al. |
| 2005/0261747 A1 | 11/2005 | Schuler et al. |
| 2005/0267347 A1 | 12/2005 | Oster |
| 2005/0288732 A1 | 12/2005 | Schuler et al. |
| 2006/0004422 A1 | 1/2006 | De Ridder |
| 2006/0017749 A1 | 1/2006 | McIntyre et al. |

(56) References Cited

U.S. PATENT DOCUMENTS

| | | |
|---|---|---|
| 2006/0020292 A1 | 1/2006 | Goetz et al. |
| 2006/0069415 A1 | 3/2006 | Cameron et al. |
| 2006/0094951 A1 | 5/2006 | Dean et al. |
| 2006/0095088 A1 | 5/2006 | De Riddler |
| 2006/0155340 A1 | 7/2006 | Schuler et al. |
| 2006/0206169 A1 | 9/2006 | Schuler |
| 2006/0218007 A1 | 9/2006 | Bjorner et al. |
| 2006/0224189 A1 | 10/2006 | Schuler et al. |
| 2006/0235472 A1 | 10/2006 | Goetz et al. |
| 2006/0259079 A1 | 11/2006 | King |
| 2006/0259099 A1 | 11/2006 | Goetz et al. |
| 2007/0000372 A1 | 1/2007 | Rezai et al. |
| 2007/0017749 A1 | 1/2007 | Dold et al. |
| 2007/0027514 A1 | 2/2007 | Gerber |
| 2007/0043268 A1 | 2/2007 | Russell |
| 2007/0049817 A1 | 3/2007 | Preiss et al. |
| 2007/0067003 A1 | 3/2007 | Sanchez et al. |
| 2007/0078498 A1 | 4/2007 | Rezai et al. |
| 2007/0083104 A1 | 4/2007 | Butson et al. |
| 2007/0123953 A1 | 5/2007 | Lee et al. |
| 2007/0129769 A1 | 6/2007 | Bourget et al. |
| 2007/0135855 A1 | 6/2007 | Foshee et al. |
| 2007/0150036 A1 | 6/2007 | Anderson |
| 2007/0156186 A1 | 7/2007 | Lee et al. |
| 2007/0162086 A1 | 7/2007 | DiLorenzo |
| 2007/0162235 A1 | 7/2007 | Zhan et al. |
| 2007/0168004 A1 | 7/2007 | Walter |
| 2007/0168007 A1 | 7/2007 | Kuzma et al. |
| 2007/0185544 A1 | 8/2007 | Dawant et al. |
| 2007/0191887 A1 | 8/2007 | Schuler et al. |
| 2007/0191912 A1 | 8/2007 | Ficher et al. |
| 2007/0197891 A1 | 8/2007 | Shachar et al. |
| 2007/0203450 A1 | 8/2007 | Berry |
| 2007/0203532 A1 | 8/2007 | Tass et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0265664 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0039895 A1 | 2/2008 | Fowler et al. |
| 2008/0071150 A1 | 3/2008 | Miesel et al. |
| 2008/0081982 A1 | 4/2008 | Simon et al. |
| 2008/0086451 A1 | 4/2008 | Torres et al. |
| 2008/0103533 A1 | 5/2008 | Patel et al. |
| 2008/0114233 A1 | 5/2008 | McIntyre et al. |
| 2008/0114579 A1 | 5/2008 | McIntyre et al. |
| 2008/0123922 A1 | 5/2008 | Gielen et al. |
| 2008/0123923 A1 | 5/2008 | Gielen et al. |
| 2008/0133141 A1 | 6/2008 | Frost |
| 2008/0141217 A1 | 6/2008 | Goetz et al. |
| 2008/0154340 A1 | 6/2008 | Goetz et al. |
| 2008/0154341 A1 | 6/2008 | McIntyre et al. |
| 2008/0163097 A1 | 7/2008 | Goetz et al. |
| 2008/0183256 A1 | 7/2008 | Keacher |
| 2008/0188734 A1 | 8/2008 | Suryanarayanan et al. |
| 2008/0215118 A1 | 9/2008 | Goetz et al. |
| 2008/0227139 A1 | 9/2008 | Deisseroth et al. |
| 2008/0242950 A1 | 10/2008 | Jung et al. |
| 2008/0261165 A1 | 10/2008 | Steingart et al. |
| 2008/0269588 A1 | 10/2008 | Csavoy et al. |
| 2008/0300654 A1 | 12/2008 | Lambert et al. |
| 2008/0300797 A1 | 12/2008 | Tabibiazar et al. |
| 2009/0016491 A1 | 1/2009 | Li |
| 2009/0054950 A1 | 2/2009 | Stephens |
| 2009/0082640 A1 | 3/2009 | Kovach et al. |
| 2009/0082829 A1 | 3/2009 | Panken et al. |
| 2009/0112289 A1 | 4/2009 | Lee et al. |
| 2009/0118635 A1 | 5/2009 | Lujan et al. |
| 2009/0118786 A1 | 5/2009 | Meadows et al. |
| 2009/0149917 A1 | 6/2009 | Whitehurst et al. |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0198354 A1 | 8/2009 | Wilson |
| 2009/0204192 A1 | 8/2009 | Carlton et al. |
| 2009/0208073 A1 | 8/2009 | McIntyre et al. |
| 2009/0210208 A1 | 8/2009 | McIntyre et al. |
| 2009/0242399 A1 | 10/2009 | Kamath et al. |
| 2009/0276008 A1 | 11/2009 | Lee et al. |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010566 A1 | 1/2010 | Thacker et al. |
| 2010/0010646 A1 | 1/2010 | Drew et al. |
| 2010/0023103 A1 | 1/2010 | Elborno |
| 2010/0023130 A1 | 1/2010 | Henry et al. |
| 2010/0030312 A1 | 2/2010 | Shen |
| 2010/0049276 A1 | 2/2010 | Blum et al. |
| 2010/0049280 A1 | 2/2010 | Goetz |
| 2010/0064249 A1 | 3/2010 | Groetken |
| 2010/0113959 A1 | 5/2010 | Pascual-Leon et al. |
| 2010/0121409 A1 | 5/2010 | Kothandaraman et al. |
| 2010/0135553 A1 | 6/2010 | Joglekar |
| 2010/0137944 A1 | 6/2010 | Zhu |
| 2010/0152604 A1 | 6/2010 | Kuala et al. |
| 2010/0179562 A1 | 7/2010 | Linker et al. |
| 2010/0324410 A1 | 12/2010 | Paek et al. |
| 2010/0331883 A1 | 12/2010 | Schmitz et al. |
| 2011/0040351 A1 | 2/2011 | Buston et al. |
| 2011/0066407 A1 | 3/2011 | Butson et al. |
| 2011/0172737 A1 | 7/2011 | Davis et al. |
| 2011/0184487 A1 | 7/2011 | Alberts et al. |
| 2011/0191275 A1 | 8/2011 | Lujan et al. |
| 2011/0196253 A1 | 8/2011 | McIntyre et al. |
| 2011/0213440 A1 | 9/2011 | Fowler et al. |
| 2011/0306845 A1 | 12/2011 | Osorio |
| 2011/0306846 A1 | 12/2011 | Osorio |
| 2011/0307032 A1 | 12/2011 | Goetz et al. |
| 2012/0027272 A1 | 2/2012 | Akinyemi et al. |
| 2012/0046715 A1 | 2/2012 | Moffitt et al. |
| 2012/0078106 A1 | 3/2012 | Dentinger et al. |
| 2012/0089205 A1 | 4/2012 | Boyden et al. |
| 2012/0116476 A1 | 5/2012 | Kothandaraman |
| 2012/0165898 A1 | 6/2012 | Moffitt |
| 2012/0165901 A1 | 6/2012 | Zhu et al. |
| 2012/0207378 A1 | 8/2012 | Gupta et al. |
| 2012/0226138 A1 | 9/2012 | DeSalles et al. |
| 2012/0229468 A1 | 9/2012 | Lee et al. |
| 2012/0265262 A1 | 10/2012 | Osorio |
| 2012/0265268 A1 | 10/2012 | Blum et al. |
| 2012/0302912 A1 | 11/2012 | Moffitt et al. |
| 2012/0303087 A1 | 11/2012 | Moffitt et al. |
| 2012/0314924 A1 | 12/2012 | Carlton et al. |
| 2012/0316619 A1 | 12/2012 | Goetz et al. |
| 2013/0039550 A1 | 2/2013 | Blum et al. |
| 2013/0060305 A1 | 3/2013 | Bokil |
| 2013/0116748 A1 | 5/2013 | Bokil et al. |
| 2013/0116749 A1 | 5/2013 | Carlton et al. |
| 2013/0116929 A1 | 5/2013 | Carlton et al. |
| 2014/0067018 A1 | 3/2014 | Carcieri et al. |

(56) References Cited

U.S. PATENT DOCUMENTS

| | | | |
|---|---|---|---|
| 2014/0277284 | A1 | 9/2014 | Chen et al. |
| 2015/0134031 | A1 | 5/2015 | Moffitt et al. |

FOREIGN PATENT DOCUMENTS

| | | |
|---|---|---|
| EP | 1372780 | 1/2004 |
| EP | 1559369 | 8/2005 |
| WO | 97/39797 | 10/1997 |
| WO | 98/48880 | 11/1998 |
| WO | 01/90876 | 11/2001 |
| WO | 02/26314 | 4/2002 |
| WO | 02/28473 | 4/2002 |
| WO | 02/065896 | 8/2002 |
| WO | 02/072192 | 9/2002 |
| WO | 03/086185 | 10/2003 |
| WO | 2004/019799 A2 | 3/2004 |
| WO | 2004041080 | 5/2005 |
| WO | 2006017053 | 2/2006 |
| WO | 2006113305 | 10/2006 |
| WO | 2007/097859 | 8/2007 |
| WO | 2007/097861 A1 | 8/2007 |
| WO | 2007/100427 | 9/2007 |
| WO | 2007/100428 | 9/2007 |
| WO | 2007/112061 | 10/2007 |
| WO | 2009097224 | 8/2009 |
| WO | 2010/120823 A2 | 10/2010 |
| WO | 2011025865 | 3/2011 |
| WO | 2011/139779 A1 | 11/2011 |
| WO | 2011/159688 A2 | 12/2011 |
| WO | 2012057951 | 5/2012 |
| WO | 2012088482 | 6/2012 |

OTHER PUBLICATIONS

U.S. Appl. No. 17/170,677, filed Feb. 8, 2021.
U.S. Appl. No. 16/284,917, filed Feb. 25, 2019.
U.S. Appl. No. 15/991,807, filed May 29, 2018.
U.S. Appl. No. 15/729,383, filed Oct. 10, 2017.
U.S. Appl. No. 15/420,842, filed Jan. 31, 2017.
U.S. Appl. No. 15/012,698, filed Feb. 1, 2016.
U.S. Appl. No. 14/011,817, filed Aug. 28, 2013.
Official Communication for U.S. Appl. No. 14/011,817, mailed Jun. 11, 2015.
Official Communication for U.S. Appl. No. 15/012,698, mailed May 5, 2016.
Official Communication for U.S. Appl. No. 15/420,842 mailed Apr. 14, 2017.
Official Communication for U.S. Appl. No. 15/420,842 mailed Jul. 13, 2017.
Official Communication for U.S. Appl. No. 15/729,383 mailed Jan. 30, 2018.
Official Communication for U.S. Appl. No. 15/991,807, mailed Aug. 30, 2018.
Official Communication for U.S. Appl. No. 16/284,917 mailed Sep. 15, 2020.
Official Communication for U.S. Appl. No. 17/170,677 mailed Sep. 15, 2022.
Official Communication for U.S. Appl. No. 18/118,660 mailed Sep. 28, 2023.
Nowinski, W. L., et al., "Statistical analysis of 168 bilateral subthalamic nucleus implantations by means of the probabilistic functional atlas.", Neurosurgery 57(4 Suppl) (Oct. 2005),319-30.
Obeso, J. A., et al., "Deep-brain stimulation of the subthalamic nucleus or the pars interna of the globus pallidus in Parkinson's disease.", N Engl J Med., 345{13l. The Deep-Brain Stimulation for Parkinson's Disease Study Group, (Sep. 27, 2001 ),956-63.
Patrick, S. K., et al., "Quantification of the UPDRS rigidity scale", IEEE Transactions on Neural Systems and Rehabilitation Engineering, [see also IEEE Trans. on Rehabilitation Engineering 9(1). (2001), 31-41.
Phillips, M. D., et al., "Parkinson disease: pattern of functional MR imaging activation during deep brain stimulation of subthalamic nucleus—initial experience", Radiology 239(1). (Apr. 2006),209-16.
Mcintyre, C. C., et al., "How does deep brain stimulation work? Present understanding and future questions.", J Clin Neurophysiol. 21 (1 ). (Jan.-Feb. 2004 ),40-50.
Plaha, P. , et al., "Stimulation of the caudal zona incerta is superior to stimulation of the subthalamic nucleus in improving contralateral parkinsonism.", Brain 129{Pt 7) (Jul. 2006), 1732-4 7.
Rattay, F, "Analysis of models for external stimulation of axons", IEEE Trans. Biomed. Eng. vol. 33 (1986),974-977.
Rattay, F., "Analysis of the electrical excitation of CNS neurons", IEEE Transactions on Biomedical Engineering 45 (6). (Jun. 1998),766-772.
Rose, T. L., et al., "Electrical stimulation with Pt electrodes. VIII. Electrochemically safe charge injection limits with 0.2 ms pulses [neuronal application]", IEEE Transactions on Biomedical Engineering, 37(11 }, (Nov. 1990), 1118-1120.
Rubinstein, J. T., et al., "Signal coding in cochlear implants: exploiting stochastic effects of electrical stimulation", Ann Otol Rhinol Laryngol Suppl. 191, (Sep. 2003), 14-9.
Schwan, H.P., et al., "The conductivity of living tissues.", Ann NY Acad Sci., 65(6). (AUQ., 1957), 1007-13.
Taylor, R. S., et al., "Spinal cord stimulation for chronic back and leg pain and failed back surgery syndrome: a systematic review and analysis of prognostic factors", Spine 30(1 ). (Jan. 1, 2005), 152-60.
Geddes, L. A., et al., "The specific resistance of biological material—a compendium of data for the biomedical engineer and physiologist.", Med Biol Ena. 5(3). (May 1967),271-93.
Gimsa, J., et al., "Choosing electrodes for deep brain stimulation experiments-electrochemical considerations.", J Neurosci Methods, 142(2), (Mar. 30, 2005),251-65.
Vioola, P., et al., "Alignment by maximization of mutual information", International Journal of Com outer Vision 24(2). ( 1997), 137-154.
Volkmann, J. , et al., "Basic algorithms for the programming of deep brain stimulation in Parkinson's disease", Mov Disord., 21 Suppl 14. (Jun. 2006),S284-9.
Walter, B. L., et al., "Surgical treatment for Parkinson's disease", Lancet Neural. 3(12). (Dec., 2004),719-28.
Wei, X. F., et al., "Current density distributions, field distributions and impedance analysis of segmented deep brain stimulation electrodes", J Neural Eng.. 2(4). (Dec. 2005), 139-47.
Zonenshayn, M. , et al., "Location of the active contact within the subthalamic nucleus (STN) in the treatment of idiopathic Parkinson's disease.", Surg Neurol., 62(3) (Sep. 2004),216-25.
Da Silva et al (A primer on diffusion tensor imaging of anatomical substructures. Neurosurg Focus 15(1): p. 1-4, Article 4, 2003.).
Micheli-Tzanakou, E., et al., "Computational Intelligence for target assesment in Parkinson's disease", Proceedings of SPIE vol. 4479. Applications and Science of Neural Networks, Fuzzy Systems, and Evolutionary Computation IV,(2001),54-69.
Grill, W. M., "Stimulus waveforms for selective neural stimulation", IEEE Engineering in Medicine and Biology Magazine, 14(4}, (Jul.-Aug. 1995), 375-385.
Miocinovic, S., et al., "Sensitivity of temporal excitation properties to the neuronal element activated by extracellular stimulation", J Neurosci Methods. 132(1). (Jan. 15, 2004), 91-9.
Hunka, K. et al., Nursing Time to Program and Assess Deep Brain Stimulators in Movement Disorder Patients, J. Neursci Nurs., 37: 204-10 (Aug. 2005).
Moss, J. , et al., "Electron microscopy of tissue adherent to explanted electrodes in dystonia and Parkinson's disease", Brain, 127{Pt 12). (Dec. 2004 ),2755-63.
Montgomery, E. B., et al., "Mechanisms of deep brain stimulation and future technical developments.", Neurol Res. 22(3). (Apr. 2000),259-66.
Merrill, D. R., et al., "Electrical stimulation of excitable tissue: design of efficacious and safe protocols", J Neurosci Methods. 141(2), (Feb. 15, 2005), 171-98.
Fisekovic et al., "New Controller for Functional Electrical Stimulation Systems", Med. Eng. Phys. 2001; 23:391-399.

(56) References Cited

OTHER PUBLICATIONS

Grill, W. M., et al., "Deep brain stimulation creates an informational lesion of the stimulated nucleus", Neuroreport. 15l7t (May 19, 2004 ), 1137-40.

Grill, WM., et al., "Electrical properties of implant encapsulation tissue", Ann Biomed Eng. vol. 22. (1994),23-33.

McNaughtan et al., "Electrochemical Issues in Impedance Tomography", 1st World Congress on Industrial Process Tomography, Buxton, Greater Manchester, Apr. 14-17, 1999.

Hardman, C. D., et al., "Comparison of the basal ganglia in rats, marmosets, macaques, baboons, and humans: volume and neuronal number for the output, internal relay, and striatal modulating nuclei", J Comp Neurol., 445(3). (Apr. 8, 2002),238-55.

Hashimoto, T. , et al., "Stimulation of the subthalamic nucleus changes the firing pattern of pallidal neurons", J Neurosci. 23(5). (Mar. 1, 2003),1916-23.

Haslinger, B., et al., "Frequency-correlated decreases of motor cortex activity associated with subthalamic nucleus stimulation in Parkinson's disease.", Neuroimage 28(3). (Nov. 15, 2005),598-606.

Haueisen, J, et al., "The influence of brain tissue anisotropy on human EEG and MEG", Neuroimage 15(1) (Jan. 2002),159-66.

Hemm, S., et al., "Deep brain stimulation in movement disorders: stereotactic coregistration of two-dimensional electrical field modeling and magnetic resonance imaging.", J Neurosurg. 103(6): (Dec. 2005),949-55.

Hemm, S. , et al., "Evolution of Brain Impedance in Dystonic Patients Treated by GPi Electrical Stimulation", Neuromodulation 7(2) (Apr. 2004),67-75.

Hershey, T., et al., "Cortical and subcortical blood flow effects of subthalamic nucleus stimulation in PD.", Neurology 61(6). (Sep. 23, 2003),816-21.

Herzog, J., et al., "Most effective stimulation site in subthalamic deep brain stimulation for Parkinson's disease", Mov Disord. 19(9). (Sep. 2004),1050-4.

Hines, M. L., et al., "The NEURON simulation environment", Neural Comput. 9(6). (Aug. 15, 1997), 1179-209.

Holsheimer, J. , et al., "Chronaxie calculated from current-duration and voltage-duration data", J Neurosci Methods. 97(1). (Apr. 1, 2000),45-50.

Johnson, M. D., et al., "Repeated voltage biasing improves unit recordings by reducing resistive tissue impedances", IEEE Transactions on Neural Systems and Rehabilitation Engineering, [see also IEEE Trans. on Rehabilitation Engineering (2005), 160-165.

Kitagawa, M., et al., "Two-year follow-up of chronic stimulation of the posterior subthalamic white matter for tremor-dominant Parkinson's disease.", Neurosurgery. 56(2). (Feb. 2005),281-9.

Limousin, P., et al., "Electrical stimulation of the subthalamic nucleus in advanced Parkinson's disease", N Engl J Med . . . 339(16), (Oct. 15, 1998), 1105-11.

Mcintyre, Cameron , et al., "Finite element analysis of the current-density and electric field generated by metal microelectrodes", Ann Biomed Eng . 29(3), (2001 ),227-235.

Mayr et al., "Basic Design and Construction of the Vienna FES Implants: Existing Solutions and Prospects for New Generations of Implants", Medical Engineering & Physics, 2001; 23:53-60.

Wakana, S., et al., "Reproducibility of quantitative tractography methods applied to cerebral white matter," Neuroimage 36 (3) (2007), pp. 630-644.

Viola, et al., "Importance-driven focus of attention," IEEE Trans Vis Comput Graph 12 (5) (2006), pp. 933-940.

Saxena, et al., "Cerebral glucose metabolism in obsessive-compulsive hoarding," Am J Psychiatry. 161 (6) (2004), pp. 1038-1048.

Volkmann et al., Indroduction to the Programming of Deep Brain Stimulators, Movement Disorders, vol. 17, Suppl. 3, pp. S181-S187 (2002).

Miocinovic et al. "Cicerone: Stereotactic Neurophysiological Recording and Deep Brain Stimulation Electrode Placement Software System," Acta Neurochirugica Suppl., Jan. 1, 2007, vol. 97, No. 2, pp. 561-567.

Butson et al.. "Current Steering to control the volume of tissue activated during deep brain stimulation," vol. 1, No. 1, Dec. 3, 2007, pp. 7-15.

Schmidt et al. "Sketching and Composing Widgets for 3D Manipulation," Eurographics, Apr. 2008, vol. 27, No. 2, pp. 301-310.

Butson et al. "Patient-Specific Analysis of the vol. of Tissue Activated During Deep Brain Stimulation." Neuroimage 34, 2007, pp. 661-670.

Ericsson, A. et al., "Construction of a patient-specific atlas of the brain: Application to normal aging," Biomedical Imaging: From Nano to Macro, ISBI 2008, 5th IEEE International Symposium, May 14, 2008, pp. 480-483.

Kaikai Shen et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.

Liliane Ramus et al., "Assessing selection methods in the cotnext of multi-atlas based segmentation," Biomedical Imaging: From Nano to Macro, 2010, IEEE International Symposium, Apr. 14, 2010, pp. 1321-1324.

Olivier Commowick et al., "Using Frankenstein's Creature Paradigm to Build a Patient Specific Atlas," Sep. 20, 2009, Medical Image Computing and Computer-Assisted Intervention, pp. 993-1000.

Lotjonen J.M.P et al., "Fast and robust multi-atlas segmentation of brain magnetic resonance images," NeuroImage, Academic Press, vol. 49, No. 3, Feb. 1, 2010, pp. 2352-2365.

Izad, Oliver, "Computationally Efficient Method in Predicating Axonal Excitation," Dissertation for Master Degree, Department of Biomedical Engineering, Case Western Reserve University, May 2009.

Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.

International Search Report and Written Opinion in International Application No. PCT/US2013/056975, dated Feb. 20, 2014.

Butson et al. "Role of Electrode Design on the Volume of Tissue Activated During Deep Brain Stimulation," Journal of Neural Engineering, Mar. 1, 2006, vol. 3, No. 1, pp. 1-8.

Butson et al. "StimExplorer: Deep Brain Stimulation Parameter Selection Software System," Acta Neurochirugica, Jan. 1, 2007, vol. 97, No. 2, pp. 569-574.

U.S. Appl. No. 12/029,141, filed Feb. 11, 2008.

Meila, Marina, "Comparing Clusterings by the Variation of Information," Learning Theory and Kernel Machines (2003): 173-187.

Cover, T.M. et al., "Elements of information theory," (1991) John Wiley & Sons, New York, NY.

Hubert, Lawrence et al., "Comparing partitions," Journal of Classification 2(1) (1985): 193-218, doi:10.1007/BF01908075.

Siegel, Ralph M. et al., "Spatiotemporal dynamics of the functional architecture for gain fields in inferior parietal lobule of behaving monkey," Cerebral Cortex, New York, NY, vol. 17, No. 2, Feb. 2007, pp. 378-390.

Klein, A. et al., "Evaluation of 14 nonlinear deformation algorithms applied to human brain MRI registration," NeuroImage, Academic Press, Orlando, FL, vol. 46, No. 3, Jul. 2009, pp. 786-802.

Rand, WM., "Objective criteria for the evaluation of clustering methods," Journal of the American Statistical Association (American Statistical Association) 66 (336) (1971 ): 846-850, doi:10.2307/2284239, http://jstor.org/stable/2284239.

Dice, Lee R., "Measures of the Amount of Ecologic Association Between Species," Ecology 26(3) (1945): 297-302. doi: 10.2307/1932409, http://jstor.org/stable/1932409.

Jaccard, Paul, "Elude comparative de la distribution florale dans une portion odes Aples et des Jura," Bulletin de la Societe Vaudoise des Sciences Naturelles (1901), 37:547-579.

Official Communication for U.S. Appl. No. 14/011,817 mailed Jun. 11, 2015, 11 pages.

Official Communication for U.S. Appl. No. 15/012,698, mailed May 5, 2016, 5 pages.

Official Communication for U.S. Appl. No. 15/991,807, mailed Aug. 30, 2018, 9 pages.

(56) References Cited

OTHER PUBLICATIONS

Zhang, Y., et al., "Atlas-guided tract reconstruction for automated and comprehensive examination of the white matter anatomy," Neuroimage 52(4) (2010), pp. 1289-1301.

"BioPSE" The Biomedical Problem Solving Environment, htt12:// www.sci.utah.edu/cibc/software/index.html, MCRR Center for Integrative Biomedical Computing,(2004).

Andrews, R. J., "Neuroprotection trek—the next generation: neuromodulation I. Techniques—deep brain stimulation, vagus nerve stimulation, and transcranial magnetic stimulation.", Ann NY Acad Sci. 993. (May 2003), 1-13.

Carnevale, N.T. et al., "The Neuron Book," Cambridge, UK: Cambridge University Press (2006), 480 pages.

Chaturvedi: "Development of Accurate Computational Models for Patient-Specific Deep Brain Stimulation," Electronic Thesis or Dissertation, Jan. 2012, 162 pages.

Chaturvedi, A. et al.: "Patient-specific models of deep brain stimulation: Influence of field model complexity on neural activation predictions." Brain Stimulation, Elsevier, Amsterdam, NL, vol. 3, No. 2 Apr. 2010, pp. 65-77.

Frankemolle, et al., "Reversing cognitive-motor impairments in Parkinson's disease patients using a computational modeling approach to deep brain stimulation programming," Brian 133 (2010), pp. 746-761.

McIntyre, C.C., et al., "Modeling the excitablitity of mammalian nerve fibers: influence of afterpotentials on the recovery cycle," J Neurophysiol, 87(2) (Feb. 2002), pp. 995-1006.

Peterson, et al., "Predicting myelinated axon activation using spatial characteristics of the extracellular field," Journal of Neural Engineering, 8 (2011), 12 pages.

Warman, et al., "Modeling the Effects of Electric Fields on nerver Fibers; Dermination of Excitation Thresholds, "IEEE Transactions on Biomedical Engineering, vol. 39, No. 12 (Dec. 1992), pp. 1244-1254.

Wesselink, et al., "Analysis of Current Density and Related Parameters in Spinal Cord Stimulation," IEEE Transactions on Rehabilitation Engineering, vol. 6, No. 12 Jun. 1998, pp. 200-207.

Andrews, R. J., "Neuroprotection trek—the next generation: neuromodulation II. Applications—epilepsy, nerve regeneration, neurotrophins.", Ann NY Acad Sci. 993 (May 2003), 14-24.

Astrom, M. , et al., "The effect of cystic cavities on deep brain stimulation in the basal ganglia: a simulation-based study", J Neural Eng., 3(2), (Jun. 2006). 132-8.

Bazin et al., "Free Software Tools for Atlas-based Volumetric Neuroimage Analysis", Proc. SPIE 5747, Medical Imaging 2005: Image Processing, 1824 May 5, 2005.

Back, C. , et al., "Postoperative Monitoring of the Electrical Properties of Tissue and Electrodes in Deep Brain Stimulation", Neuromodulation, 6(4), (Oct. 2003 ),248-253.

Baker, K. B., et al., "Evaluation of specific absorption rate as a dosimeter of MRI-related implant heating", J Magn Reson Imaging., 20(2), (Aug. 2004), 315-20.

Brown, J. " Motor Cortex Stimulation," Neurosurgical Focus ( Sep. 15, 2001) 11(3):E5.

Budai et al., "Endogenous Opioid Peptides Acting at m-Opioid Receptors in the Dorsal Horn Contribute to Midbrain Modulation of Spinal Nociceptive Neurons," Journal of Neurophysiology (1998) 79(2): 677-687.

Cesselin, F. "Opioid and anti-opioid peptides," Fundamental and Clinical Pharmacology (1995) 9(5): 409-33 (Abstract only).

Rezai et al., "Deep Brain Stimulation for Chronic Pain" Surgical Management of Pain, Chapter 44 pp. 565-576 (2002).

Xu, MD., Shi-Ang, article entitled "Comparison of Half-Band and Full-Band Electrodes for Intracochlear Electrical Stimulation", Annals of Otology, Rhinology & Laryngology (Annals of Head & Neck Medicine & Surgery), vol. 102 (5) pp. 363-367 May 1993.

Bedard, C. , et al., "Modeling extracellular field potentials and the frequency-filtering properties of extracellular space", Biophys J . . . 86(3). (Mar. 2004), 1829-42.

Benabid, A. L., et al., "Future prospects of brain stimulation", Neurol Res.;22(3), (Apr. 2000),237-46.

Brummer, S. B., et al., "Electrical Stimulation with Pt Electrodes: II—Estimation of Maximum Surface Redox (Theoretical Non-Gassing) Limits", IEEE Transactions on Biomedical Engineering, Volume BME-24, Issue 5, (Sep. 1977),440-443.

Butson, Christopher R., et al., "Deep Brain Stimulation of the Subthalamic Nucleus: Model-Based Analysis of the Effects of Electrode Capacitance on the Volume of Activation", Proceedings of the 2nd International IEEE EMBS, (Mar. 16-19, 2005), 196-197.

Mcintyre, Cameron C., et al., "Cellular effects of deep brain stimulation: model-based analysis of activation and inhibition," J Neurophysiol, 91(4) (Apr. 2004), pp. 1457-1469.

Chaturvedi, A., et al., "Subthalamic Nucleus Deep Brain Stimulation: Accurate Axonal Threshold Prediction with Diffusion Tensor Based Electric Field Models", Engineering in Medicine and Biology Society, 2006. EMBS' 06 28th Annual International Conference of the IEEE, IEEE, Piscataway, NJ USA, Aug. 30, 2006.

Butson, Christopher et al., "Predicting the Effects of Deep Brain Stimulation with Diffusion Tensor Based Electric Field Models" Jan. 1, 2001, Medical Image Computing and Computer-Assisted Intervention-Mic CAI 2006 Lecture Notes in Computer Science; LNCS, Springer, Berlin, DE.

Butson, C. R., et al., "Deep brainstimulation interactive visualization system", Society for Neuroscience vol. 898.7 (2005).

Hodaie, M., et al., "Chronic anterior thalamus stimulation for intractable epilepsy," Epilepsia, 43(6) (Jun. 2002), pp. 603-608.

Hoekema, R., et al., "Multigrid solution of the potential field in modeling electrical nerve stimulation," Comput Biomed Res., 31(5) (Oct. 1998), pp. 348-362.

Holsheimer, J., et al., "Identification of the target neuronal elements in electrical deep brain stimulation," Eur J Neurosci., 12(12) (Dec. 2000), pp. 4573-4577.

Jezernik, S., et al., "Neural network classification of nerve activity recorded in a mixed nerve," Neurol Res., 23(5) (Jul. 2001), pp. 429-434.

Jones, DK., et al., "Optimal strategies for measuring diffusion in anisotropic systems by magnetic resonance imaging," Magn. Reson. Med., 42(3) (Sep. 1999), pp. 515-525.

Krack, P., et al., "Postoperative management of subthalamic nucleus stimulation for Parkinson's disease," Mov. Disord., vol. 17(suppl 3) (2002), pp. 188-197.

Le Bihan, D., et al., "Diffusion tensor imaging: concepts and applications," J Magn Reson Imaging, 13(4) (Apr. 2001), pp. 534-546.

Lee, D. C., et al., "Extracellular electrical stimulation of central neurons: quantitative studies," In: Handbook of neuroprosthetic methods, WE Finn and PG Lopresti (eds) CRC Press (2003), pp. 95-125.

Levy, AL., et al., "An Internet-connected, patient-specific, deformable brain atlas integrated into a surgical navigation system," J Digit Imaging, 10(3 Suppl 1) (Aug. 1997), pp. 231-237.

Liu, Haiying, et al., "Intra-operative MR-guided DBS implantation for treating PD and ET," Proceedings of SPIE vol. 4319, Department of Radiology & Neurosurgery, University of Minnesota, Minneapolis, MN 55455 (2001), pp. 272-276.

Mcintyre, C. C., et al., "Extracellular stimulation of central neurons: influence of stimulus waveform and frequency on neuronal output," J. Neurophysiol., 88(4), (Oct. 2002), pp. 1592-1604.

Mcintyre, C. C., et al., "Microstimulation of spinal motoneurons: a model study," Proceedings of the 19th Annual International Conference of the IEEE Engineering in Medicine and Biology society, vol. 5, (1997), pp. 2032-2034.

Mcintyre, Cameron C., et al., "Model-based Analysis of deep brain stimulation of the thalamus," Proceedings of the Second joint EMBS/BM ES Conference, vol. 3, Annual Fall Meeting of the Biomedical Engineering Society (Cal. No. 02CH37392) IEEEPiscataway, NJ (2002), pp. 2047-2048.

Mcintyre, C. C., et al., "Model-based design of stimulus trains for selective microstimulation of targeted neuronal populations," Proceedings of the 23rd Annual International Conference of the IEEE Engineering in Medicine and Biology Society, vol. 1 (2001), pp. 806-809.

(56) References Cited

OTHER PUBLICATIONS

Mcintyre, C. C., et al., Model-based design of stimulus waveforms for selective microstimulation in the central nervous system,, Proceedings of the First Joint [Engineering in Medicine and Biology, 1999. 21st Annual Conf. and the 1999 Annual FallMeeting of the Biomedical Engineering Soc.] BM ES/EMBS Conference, vol. 1 (1999), p. 384.

Mcintyre, Cameron C., et al., "Modeling the excitability of mammalian nerve fibers: influence of afterpotentials on the recovery cycle," J Neurophysiol, 87(2) (Feb. 2002), pp. 995-1006.

Mcintyre, Cameron C., et al., "Selective microstimulation of central nervous system neurons," Annals of biomedical engineering, 28(3) (Mar. 2000), pp. 219-233.

Mcintyre, C. C., et al., "Sensitivity analysis of a model of mammalian neural membrane," Biol Cybern., 79(1) (Jul. 1998), pp. 29-37.

Mcintyre, Cameron C., et al., "Uncovering the mechanism(s) of action of deep brain stimulation: activation, inhibition, or both," Clin Neurophysiol, 115(6) (Jun. 2004), pp. 1239-1248.

Mcintyre, Cameron C., et al., "Uncovering the mechanisms of deep brain stimulation for Parkinson's disease through functional imaging, neural recording, and neural modeling," Crit Rev Biomed Eng., 30(4-6) (2002), pp. 249-281.

Mouine et al. "Multi-Strategy and Multi-Algorithm Cochlear Prostheses", Biomed. Sci. Instrument, 2000; 36:233-238.

Mcintyre, Cameron C., et al., "Electric Field and Stimulating Influence generated by Deep Brain Stimulation of the Subthalamaic Nucleus," Clinical Neurophysiology, 115(3) (Mar. 2004), pp. 589-595.

Mcintyre, Cameron C., et al., "Electric field generated by deep brain stimulation of the subthalamic nucleus," Biomedical Engineering Society Annual Meeting, Nashville TN (Oct. 2003), 16 pages.

Mcintyre, Cameron C., et al., "Excitation of central nervous system neurons by nonuniform electric fields," Biophys. J., 76(2) (1999), pp. 878-888.

McNeal, DR., et al., "Analysis of a model for excitation of myelinated nerve," IEEE Trans Biomed Eng., vol. 23 (1976), pp. 329-337.

Micheli-Tzanakou, E. , et al., "Computational Intelligence for target assesment in Parkinson's disease," Proceedings of SPIE vol. 4479, Applications and Science of Neural Networks, Fuzzy Systems, and Evolutionary Computation IV (2001 ), pp. 54-69.

Miocinovic, S., et al., "Computational analysis of subthalamic nucleus and lenticular fasciculus activation during therapeutic deep brain stimulation," J Neurophysiol., 96(3) (Sep. 2006), pp. 1569-1580.

Miranda, P. C., et al., "The distribution of currents inducedin the brain by Magnetic Stimulation: a finite element analysis incorporating OT-MRI-derived conductivity data," Proc. Intl. Soc. Mag. Reson. Med. 9 (2001 ), p. 1540.

Miranda, P. C., et al., "The Electric Field Induced in the Brain by Magnetic Stimulation: A 3-D Finite-Element Analysis of the Effect of Tissue Heterogeneity and Anisotropy," IEEE Transactions on Biomedical Enginering, 50(9) (Sep. 2003), pp. 1074-1085.

Moffitt, MA., et al., "Prediction of myelinated nerve fiber stimulation thresholds: limitations of linear models," IEEE Transactions on Biomedical Engineering, 51 (2) (2003), pp. 229-236.

Moro, E, et al., "The impact on Parkinson's disease of electrical parameter settings in STN stimulation," Neurology, 59 (5) (Sep. 10, 2002), pp. 706-713.

Nowak, LG., et al., "Axons, but not cell bodies, are activated by electrical stimulation in cortical gray matter. I. Evidence from chronaxie measurements," Exp. Brain Res., 118(4) (Feb. 1998), pp. 477-488.

Nowak, LG., et al., "Axons, but not cell bodies, are activated by electrical stimulation in cortical gray matter. II. Evidence from selective inactivation of cell bodies and axon initial segments," Exp. Brain Res., 118(4) (Feb. 1998), pp. 489-500.

O'Suilleabhain, PE., et al., "Tremor response to polarity, voltage, pulsewidth and frequency of thalamic stimulation," Neurology, 60(5) (Mar. 11, 2003), pp. 786-790.

Pierpaoli, C., et al., "Toward a quantitative assessment of diffusion anisotropy," Magn Reson Med., 36(6) (Dec. 1996), pp. 893-906.

Plonsey, R., et al., "Considerations of quasi-stationarity in electrophysiological systems," Bull Math Biophys., 29(4) (Dec. 1967), pp. 657-664.

Ranck, J B., "Specific impedance of rabbit cerebral cortex," Exp. Neurol., vol. 7 (Feb. 1963), pp. 144-152.

Ranck, J B., et al., "The Specific impedance of the dorsal columns of the cat: an anisotropic medium," Exp. Neurol., 11 (Apr. 1965), pp. 451-463.

Ranck, J B., "Which elements are excited in electrical stimulation of mammalian central nervous system: a review," Brain Res., 98(3) (Nov. 21, 1975), pp. 417-440.

Rattay, F., et al., "A model of the electrically excited human cochlear neuron. I. Contribution of neural substructures to the generation and propagation of spikes," Hear Res., 153(1-2) (Mar. 2001), pp. 43-63.

Rattay, F., "A model of the electrically excited human cochlear neuron. II. Influence of the three-dimensional cochlear structure on neural excitability," Hear Res., 153(1-2) (Mar. 2001), pp. 64-79.

Rattay, F., "Arrival at Functional Electrostimulation by modelling of fiber excitation," Proceedings of the Ninth annual Conference of the IEEE Engineering in Medicine and Biology Society (1987), pp. 1459-1460.

Rattay, F., "The influence of intrinsic noise can preserve the temporal fine structure of speech signals in models of electrically stimulated human cochlear neurones," Journal of Physiology, Scientific Meeting of the Physiological Society, London, England, UK Apr. 19-21, 1999 (Jul. 1999), p. 170P.

Rizzone, M., et al., "Deep brain stimulation of the subthalamic nucleus in Parkinson's disease: effects of variation in stimulation parameters," J. Neurol. Neurosurg. Psychiatry., 71(2) (Aug. 2001), pp. 215-219.

Saint-Cyr, J. A., et al., "Localization of clinically effective stimulating electrodes in the human subthalamic nucleus on magnetic resonance imaging," J. Neurosurg., 87(5) (Nov. 2002), pp. 1152-1166.

Sances, A., et al., "In Electroanesthesia: Biomedical and Biophysical Studies," A Sances and SJ Larson, Eds., Academic Press, NY (1975), pp. 114-124.

SI. Jean, P., et al., "Automated atlas integration and interactive three-dimensional visualization tools for planning and guidance in functional neurosurgery," IEEE Transactions on Medical Imaging, 17(5) (1998), pp. 672-680.

Starr, P.A., et al., "Implantation of deep brain stimulators into the subthalamic nucleus: technical approach and magnetic resonance imaging-verified lead locations," J. Neurosurg., 97(2) (Aug. 2002), pp. 370-387.

Sterio, D., et al., "Neurophysiological refinement of subthalamic nucleus targeting," Neurosurgery, 50(1) (Jan. 2002), pp. 58-69.

Struijk, J. J., et al., "Excitation of dorsal root fibers in spinal cord stimulation: a theoretical study," IEEE Transactions on Biomedical Engineering, 40(7) (Jul. 1993), pp. 632-639.

Struijk, J J., et al., "Recruitment of dorsal column fibers in spinal cord stimulation: influence of collateral branching," IEEE Transactions on Biomedical Engineering, 39(9) (Sep. 1992), pp. 903-912.

Tamma, F., et al., "Anatomo-clinical correlation of intraoperative stimulation-induced side-effects during HF-DBS of the subthalamic nucleus," Neurol Sci., vol. 23 (Suppl 2) (2002), pp. 109-110.

Tarler, M., et al., "Comparison between monopolar and tripolar configurations in chronically implanted nerve cuff electrodes," IEEE 17th Annual Conference Engineering in Medicine and Biology Society, vol. 2 (1995), pp. 1093-1109.

Testerman, Roy L., "Coritical response to callosal stimulation: A model for determining safe and efficient stimulus parameters," Annals of Biomedical Engineering, 6(4) (1978), pp. 438-452.

Tuch, D.S., et al., "Conductivity mapping of biological tissue using diffusion MRI," Ann NY Acad Sci., 888 (Oct. 30, 1999), pp. 314-316.

Tuch, D.S., et al., "Conductivity tensor mapping of the human brain using diffusion tensor MRI," Proc Nall Acad Sci USA, 98(20) (Sep. 25, 2001), pp. 11697-11701.

(56) References Cited

OTHER PUBLICATIONS

Veraart, C., et al., "Selective control of muscle activation with a multipolar nerve cuff electrode," IEEE Transactions on Biomedical Engineering, 40(7) (Jul. 1993), pp. 640-653.
Vercueil, L., et al., "Deep brain stimulation in the treatment of severe dystonia," J. Neurol., 248(8) (Aug. 2001 ), pp. 695-700.
Vilalte, "Circuit Design of the Power-on-Reset," Apr. 2000, pp. 1-25.
Vitek, J. L., "Mechanisms of deep brain stimulation: excitation or inhibition," Mov. Disord., vol. 17 (Suppl. 3) (2002), pp. 69-72.
Voges, J., et al., "Bilateral high-frequency stimulation in the subthalamic nucleus for the treatment of Parkinson disease: correlation of therapeutic effect with anatomical electrode position," J. Neurosurg., 96(2) (Feb. 2002), pp. 269-279.
Wakana, S., et al., "Fiber tract-based atlas of human white matter anatomy," Radiology, 230(1) (Jan. 2004), pp. 77-87.
Alexander, DC., et al., "Spatial transformations of diffusion tensor magnetic resonance images," IEEE Transactions on Medical Imaging, 20 (11), (2001), pp. 1131-1139.
Wu, Y. R., et al., "Does Stimulation of the GPi control dyskinesia by activating inhibitory axons?," Mov. Disord., vol. 16 (2001), pp. 208-216.
Yelnik, J., et al., "Localization of stimulating electrodes in patients with Parkinson disease by using a three-dimensional atlas-magnetic resonance imaging coregistration method," J Neurosurg., 99(1) (Jul. 2003), pp. 89-99.
Manni, John, et al., "Globus pallidus internus deep brain stimulation for dystonic conditions: a prospective audit," Mov. Disord., vol. 18 (2003), pp. 436-442.
Zonenshayn, M., et al., "Comparison of anatomic and neurophysiological methods for subthalamic nucleus targeting," Neurosurgery, 47(2) (Aug. 2000), pp. 282-294.
Voghell et al., "Programmable Current Source Dedicated to Implantable Microstimulators" ICM '98 Proceedings of the Tenth International Conference, pp. 67-70.
Butson, Christopher R. , et al., "Patient-specific analysis of the volume of tissue activated during deep brain stimulation", NeuroImage. vol. 34 (2007), 661-670.
Adler, DE., et al., "The tentorial notch: anatomical variation, morphometric analysis, and classification in 100 human autopsy cases," J. Neurosurg., 96(6), (Jun. 2002), pp. 1103-1112.
Jones et al., "An Advanced Demultiplexing System for Physiological Stimulation", IEEE Transactions on Biomedical Engineering, vol. 44 No. 12 Dec. 1997, pp. 1210-1220.
Butson et al., "Tissue and Electrode Capacitance Reduce Neural Activation Volumes. During Deep Brain Stimulation", Clinical Neurophysiology, 116:2490-2500, Oct. 2005.
Butson et al., "Sources and Effects of Electrode Impedance During Deep Brain Stimulation", Clinical Neurophysiology, 117:44 7-454, Dec. 2005.
D'Haese et al., "Computer-Aided Placement of Deep Brain Stimulators: From Planning to Intraoperative Guidance", IEEE Transaction on Medical Imaging, 24:1469-1478, Nov. 2005.
Gross et al., "Electrophysiological Mapping for the Implantation of Deep Brain Stimulators for Parkinson's Disease and Tremor", Movement Disorders, 21 :S259-S283, Jun. 2006.
Halpern et al., "Brain Shift During Deep Brain Stimulation Surgery for Parkinson's Disease", Stereotact Funct. Neurosurg., 86:37-43, published online Sep. 2007.
Herzog et al., "Most Effective Stimulation Site in Subthalamic Deep Brain Stimulation for Parkinson's Disease", Movement Disorders, 19:1050-1099, published on line Mar. 2004.
Jeon et al., A Feasibility Study of Optical Coherence Tomography for Guiding Deep Brain Probes, Journal of Neuroscience Methods, 154:96-101, Jun. 2006.
Khan et al., "Assessment of Brain Shift Related to Deep Brain Stimulation Surgery", Sterreotact Funct. Neurosurg., 86:44-53, published online Sep. 2007.
Koop et al., "Improvement in a Quantitative Measure of Bradykinesia After Microelectrode Recording in Patients with Parkinson's Disease During Deep Brain Stimulation Surgery", Movement Disorders, 21 :673-678, published on line Jan. 2006.
Lemaire et al., "Brain Mapping in Stereotactic Surgery: A Brief Overview from the Probabilistic Targeting to the Patient-Based Anatomic Mapping", NeuroImage, 37:S109-S115, available online Jun. 2007.
Machado et al., "Deep Brain Stimulation for Parkinson's Disease: Surgical Technique and Perioperative Management", Movement Disorders, 21 :S247-S258, Jun. 2006.
Maks et al., "Deep Brain Stimulation Activation Volumes and Their Association with Neurophysiological Mapping and Therapeutic Outcomes", Downloaded from jnnp.bmj.com, pp. 1-21, published online Apr. 2008.
Moran et al., "Real-Time Refinment of Subthalamic Nucleous Targeting Using Bayesian Decision-Making on the Root Mean Square Measure", Movement Disorders, 21: 1425-1431, published online Jun. 2006.
Sakamoto et al., "Homogeneous Fluorescence Assays for RNA Diagnosis by Pyrene-Conjugated 2'-0-Methyloligoribonucleotides", Nucleosides, Nucleotides, and Nucleric Acids, 26:1659-1664, on line publication Oct. 2007.
Winkler et al., The First Evaluation of Brain Shift During Functional Neurosurgery by Deformation Field Analysis, J. Neural. Neurosurg. Psychiatry, 76:1161-1163, Aug. 2005.
Yelnik et al., "A Three-Dimensional, Histological and Deformable Atlas of the Human Basal J Ganglia. I. Atlas Construction Based on Immunohistochemical and MRI Data", NeuroImage, 34:618,-638, Jan. 2007.
Ward, H. E., et al., "Update on deep brain stimulation for neuropsychiatric disorders," Neurobiol Dis 38 (3) (2010), pp. 346-353.
Alberts et al. "Bilateral subthalamic stimulation impairs cognitive-motor performance in Parkinson's disease patients." Brain (2008), 131, 3348-3360, Abstract.
Butson, Christopher R., et al., "Sources and effects of electrode impedance during deep brain stimulation", Clinical Neurophysiology. vol. 117.(2006), 447-454.
An, et al., "Prefrontal cortical projections to longitudinal columns in the midbrain periaqueductal gray in macaque monkeys," J Comp Neural 401 (4) (1998), pp. 455-479.
Bulson, C. R., et al., "Tissue and electrode capacitance reduce neural activation volumes during deep brain stimulation," Clinical Neurophysiology, vol. 116 (2005), pp. 2490-2500.
Carmichael, S. T., et al., "Connectional networks within the orbital and medial prefrontal cortex of macaque monkeys," J Comp Neural 371 (2) (1996), pp. 179-207.
Croxson, et al., "Quantitative investigation of connections of the prefrontal cortex in the human and macaque using probabilistic diffusion tractography," J Neurosci 25 (39) (2005), pp. 8854-8866.
Frankemolle, et al., "Reversing cognitive-motor impairments in Parkinson's disease patients using a computational modelling approach to deep brain stimulation programming," Brain 133 (2010), pp. 746-761.
Freedman, et al., "Subcortical projections of area 25 (subgenual cortex) of the macaque monkey," J Comp Neurol 421 (2) (2000), pp. 172-188.
Giacobbe, et al., "Treatment resistant depression as a failure of brain homeostatic mechanisms: implications for deep brain stimulation," Exp Neural 219 (1) (2009), pp. 44-52.
Goodman, et al., "Deep brain stimulation for intractable obsessive compulsive disorder: pilot study using a blinded, staggered-onset design," Biol Psychiatry 67 (6) (2010), pp. 535-542.
Greenberg, et al., "Deep brain stimulation of the ventral internal capsule/ventral striatum for obsessive-compulsive disorder: worldwide experience," Mol Psychiatry 15 (1) (2010), pp. 64-79.
Greenberg et al., "Three-year outcomes in deep brain stimulation for highly resistant obsessive-compulsive disorder," Neuropsychopharmacology 31 (11) (2006), pp. 2384-2393.
Gutman, et al., "A tractography analysis of two deep brain stimulation white matter targets for depression," Biol Psychiatry 65 (4) (2009), pp. 276-282.

(56) References Cited

OTHER PUBLICATIONS

Haber, et al., "Reward-related cortical inputs define a large striatal region in primates that interface with associative cortical connections, providing a substrate for incentive-based learning," J Neurosci 26 (32) (2006), pp. 8368-8376.
Haber, et al., "Cognitive and limbic circuits that are affected by deep brain stimulation," Front Biosci 14 (2009), pp. 1823-1834.
Hines, M. L., et al., "The NEURON simulation environment," Neural Comput., 9(6) (Aug. 15, 1997), pp. 1179-1209.
Hua, et al., "Tract probability maps in stereotaxic spaces: analyses of white matter anatomy and tract-specific quantification," Neuroimage 39 (1) (2008), pp. 336-347.
Johansen-Berg, et al., "Anatomical connectivity of the subgenual cingulate region targeted with deep brain stimulation for treatment-resistant depression," Cereb Cortex 18 (6) (2008), pp. 1374-1383.
Kopell, et al., "Deep brain stimulation for psychiatric disorders," J Clin Neurophysiol 21 (1) (2004), pp. 51-67.
Lozano, et al., "Subcallosal cingulate gyrus deep brain stimulation for treatment-resistant depression," Biol Psychiatry 64 (6) (2008), pp. 461-467.
Lujan, et al., "Tracking the mechanisms of deep brain stimulation for neuropsychiatric disorders," Front Biosci 13 (2008), pp. 5892-5904.
Lujan, J.L. et al., "Automated 3-Dimensional Brain Atlas Fitting to Microelectrode Recordings from Deep Brain Stimulation Surgeries," Stereotact. Func!. Neurosurg. 87(2009), pp. 229-240.
Machado et al., "Functional topography of the ventral striatum and anterior limb of the internal capsule determined by electrical stimulation of awake patients," Clin Neurophysiol 120 (11) (2009), pp. 1941-1948.
Malone, et al., "Deep brain stimulation of the ventral capsule/ventral striatum for treatment-resistant depression," Biol Psychiatry 65 (4) (2009), pp. 267-275.
Mayberg, H. S., et al., "Deep brain stimulation for treatment-resistant depression," Neuron, 45(5) (Mar. 3, 2005), pp. 651-660.
Mayberg, H. S., et al., "Limbic-cortical dysregulation: a proposed model of depression," J Neuropsychiatry Clin Neurosci. 9 (3) (1997), pp. 471-481.
McIntyre,C. C., et al., "Network perspectives on the mechanisms of deep brain stimulation," Neurobiol Dis 38 (3) (2010), pp. 329-337.
Miocinovic, S., et al., "Experimental and theoretical characterization of the voltage distribution generated by deep brain stimulation," Exp Neurol 216 (i) (2009), pp. 166-176.
Nuttin, et al., "Electrical stimulation in anterior limbs of internal capsules in patients with obsessive-compulsive disorder," Lancet 354 (9189) (1999), p. 1526.
Pulliam CL, Heldman DA, Orcutt TH, Mera TO, Giuffrida JP, Vitek JL. Motion sensor strategies for automated optimization of deep brain stimulation in Parkinson's disease. Parkinsonism Relat Disord. Apr. 2015; 21(4):378-82.
Alo, K. M., et al., "New trends in neuromodulation for the management of neuropathic pain," Neurosurgery, 50(4), (Apr. 2002), pp. 690-703, discussion pp. 703-704.
Ashby, P., et al., "Neurophysiological effects of stimulation through electrodes in the human subthalamic nucleus," Brain, 122 (PI 10), (Oct. 1999), pp. 1919-1931.
Baker, K. B., et al., "Subthalamic nucleus deep brain stimulus evoked potentials: Physiological and therapeutic implications," Movement Disorders, 17(5), (Sep./Ocl. 2002), pp. 969-983.
Bammer, R, et al., "Diffusion tensor imaging using single-shot SENSE-EPI", Magn Reson Med., 48(1 ), (Jul. 2002), pp. 128-136.
Basser, P J., et al., "MR diffusion tensor spectroscopy and imaging," Biophys J., 66(1 ), (Jan. 1994), pp. 259-267.
Basser, P J., et al., "New currents in electrical stimulation of excitable tissues," Annu Rev Biomed Eng., 2, (2000), pp. 377-397.
Benabid, AL., et al., "Chronic electrical stimulation of the ventralis intermedius nucleus of the thalamus as a treatment of movement disorders," J. Neurosurg., 84(2), (Feb. 1996), pp. 203-214.
Benabid, AL., et al., "Combined (Ihalamotoy and stimulation) stereotactic surgery of the VIM thalamic nucleus for bilateral Parkinson disease," Appl Neurophysiol, vol. 50, (1987), pp. 344-346.
Benabid, A L., et al., "Long-term suppression of tremor by chronic stimulation of the ventral intermediate thalamic nucleus," Lancet, 337 (8738), (Feb. 16, 1991 ), pp. 403-406.
Butson, C. R., et al., "Predicting the effects of deep brain stimulation with diffusion tensor based electric field models," Medical Image Computing and Computer-Assisted Intervention—Mic Cai 2006, Lecture Notes in Computer Science (LNCS), vol. 4191, pp. 429-437, LNCS, Springer, Berlin, DE.
Christensen, Gary E., et al., "Volumetric transformation of brain anatomy," IEEE Transactions on Medical Imaging, 16 (6), (Dec. 1997), pp. 864-877.
Cooper, S , et al., "Differential effects of thalamic stimulation parameters on tremor and paresthesias in essential tremor," Movement Disorders, 17(Supp. 5), (2002), p. S193.
Coubes, P, et al., "Treatment of DYT1-generalised dystonia by stimulation of the internal globus pallidus," Lancet, 355 (9222), (Jun. 24, 2000), pp. 2220-2221.
Dasilva, A.F. M., et al., "A Primer Diffusion Tensor Imaging of Anatomical Substructures," Neurosurg. Focus; 15(1) (Jul. 2003), pp. 1-4.
Dawant, B. M., et al., "Compuerized atlas-guided positioning of deep brain stimulators: a feasibility study," Biomedical Image registration, Second International Workshop, WBIR 2003, Revised Papers (Lecture notes in Comput. Sci. vol. (2717), Springer-Verlag Berlin, Germany(2003), pp. 142-150.
Finnis, K. W., et al., "3-D functional atlas of subcortical structures for image guided stereotactic neurosurgery," Neuroimage, vol. 9, No. 6, Iss. 2 (1999), p. S206.
Finnis, K. W., et al., "3D Functional Database of Subcorticol Structures for Surgical Guidance in Image Guided Stereotactic Neurosurgery," Medical Image Computing and Computer-Assisted Intervention—MICCAI'99, Second International Conference. Cambridge, UK, Sep. 19-22, 1999, Proceedings (1999), pp. 758-767.
Finnis, K. W., et al., "A 3-Dimensional Database of Deep Brain Functional Anatomy, and Its Application to Image-Guided Neurosurgery," Proceedings of the Third International Conference on Medical Image Computing and Computer-Assisted Intervention. Lecture Notes In Computer Science; vol. 1935 (2000), pp. 1-8.
Finnis, K. W., et al., "A functional database for guidance of surgical and therapeutic procedures in the deep brain," Proceedings of the 22nd Annual International Conference of the IEEE Engineering in Medicine and Biology Society, vol. 3 (2000), pp. 1787-1789.
Finnis, K. W., et al., "Application of a Population Based Electrophysiological Database to the Planning and Guidance of Deep Brain Stereotactic Neurosurgery," Proceedings of the 5th International Conference on Medical Image Computing and Computer-Assisted Intervention—Part 11, Lecture Notes In Computer Science; vol. 2489 (2002), pp. 69-76.
Finnis, K. W., et al., "Subcortical physiology deformed into a patient-specific brain atlas for image-guided stereotaxy," Proceedings of SPIE—vol. 4681 Medical Imaging 2002: Visualization, Image-Guided Procedures, and Display (May 2002), pp. 184-195.
Finnis, Krik W., et al., "Three-Dimensional Database of Subcortical Electrophysiology for Image-Guided Stereotatic Functional Neurosurgery," IEEE Transactions on Medical Imaging, 22(1) (Jan. 2003), pp. 93-104.
Gabriels, L , et al., "Deep brain stimulation for treatment-refractory obsessive-compulsive disorder: psychopathological and neuropsychological outcome in three cases," Acta Psychiatr Scand., 107(4) (2003), pp. 275-282.
Gabriels, LA., et al., "Long-term electrical capsular stimulation in patients with obsessive-compulsive disorder," Neurosurgery, 52(6) (Jun. 2003), pp. 1263-1276.
Goodall, E. V., et al., "Modeling study of activation and propagation delays during stimulation of peripheral nerve fibers with a tripolar cuff electrode," IEEE Transactions on Rehabilitation Engineering, [see also IEEE Trans. on Neural Systems and Rehabilitation], 3(3) (Sep. 1995), pp. 272-282.

(56) References Cited

OTHER PUBLICATIONS

Goodall, E. V., et al., "Position-selective activation of peripheral nerve fibers with a cuff electrode," IEEE Transactions on Biomedical Engineering, 43(8) (Aug. 1996), pp. 851-856.

Goodall, E. V., "Simulation of activation and propagation delay during tripolar neural stimulation," Proceedings of the 15th Annual International Conference of the IEEE Engineering in Medicine and Biology Society (1993), pp. 1203-1204.

Grill, WM., "Modeling the effects of electric fields on nerve fibers: influence of tissue electrical properties," IEEE Transactions on Biomedical Engineering, 46(8) (1999), pp. 918-928.

Grill, W. M., et al., "Neural and connective tissue response to long-term implantation of multiple contact nerve cuff electrodes," J Biomed Mater Res., 50(2) (May 2000), pp. 215-226.

Grill, W. M., "Neural modeling in neuromuscular and rehabilitation research," Proceedings of the 23rd Annual International Conference of the IEEE Engineering in Medicine and Biology Society, vol. 4 (2001 ), pp. 4065-4068.

Grill, W. M., et al., "Non-invasive measurement of the input-output properties of peripheral nerve stimulating electrodes," Journal of Neuroscience Methods, 65(1) (Mar. 1996), pp. 43-50.

Grill, W. M., et al., "Quantification of recruitment properties of multiple contact cuff electrodes," IEEE Transactions on Rehabilitation Engineering, [see also IEEE Trans. on Neural Systems and Rehabilitation], 4(2) (Jun. 1996), pp. 49-62.

Grill, W. M., "Spatially selective activation of peripheral nerve for neuroprosthetic applications," Ph.D. Case Western Reserve University, (1995), pp. 245 pages.

Grill, W. M., "Stability of the input-output properties of chronically implanted multiple contact nerve cuff stimulating electrodes," IEEE Transactions on Rehabilitation Engineering [see also IEEE Trans. on Neural Systems and Rehabilitation] (1998), pp. 364-373.

Grill, W. M., "Stimulus waveforms for selective neural stimulation," IEEE Engineering in Medicine and Biology Magazine, 14(4) (Jul.-Aug. 1995), pp. 375-385.

Grill, W. M., et al., "Temporal stability of nerve cuff electrode recruitment properties," IEEE 17th Annual Conference Engineering in Medicine and Biology Society, vol. 2 (1995), pp. 1089-1090.

Gross, RE., et al., "Advances in neurostimulation for movement disorders," Neurol Res., 22(3) (Apr. 2000), pp. 247-258.

Guridi et al., "The subthalamic nucleus, hemiballismus and Parkinson's disease: reappraisal of a neurological dogma," Brain, vol. 124, 2001, pp. 5-19.

Haberler, C, et al., "No tissue damage by chronic deep brain stimulation in Parkinson's disease," Ann Neurol., 48(3) (Sep. 2000), pp. 372-376.

Hamel, W, et al., "Deep brain stimulation of the subthalamic nucleus in Parkinson's disease: evaluation of active electrode contacts," J Neurol Neurosurg Psychiatry, 74(8) (Aug. 2003), pp. 1036-1046.

Hanekom, "Modelling encapsulation tissue around cochlear implant electrodes," Med. Biol. Eng. Comput. vol. 43 (2005), pp. 47-55.

Haueisen, J , et al., "The influence of brain tissue anisotropy on human EEG and MEG," Neuroimage, 15(1) (Jan. 2002), pp. 159-166.

D'Haese et al. Medical Image Computing and Computer-Assisted Intervention—MICCAI 2005 Lecture Notes in Computer Science, 2005, vol. 3750, 2005, 427-434.

Rohde et al. IEEE Transactions on Medical Imaging, vol. 22 No. 11, 2003 p. 1470-1479.

Dawant et al., Biomedical Image Registration. Lecture Notes in Computer Science, 2003, vol. 2717, 2003, 142-150.

Miocinovic et al., "Stereotactiv Neurosurgical Planning, Recording, and Visualization for Deep Brain Stimulation in Non-Human Primates", Journal of Neuroscience Methods, 162:32-41, Apr. 5, 2007, XP022021469.

Gemmar et al., "Advanced Methods for Target Navigation Using Microelectrode Recordings in Stereotactic Neurosurgery for Deep Brain Stimulation", 21st IEEE International Symposium on Computer-Based Medical Systems, Jun. 17, 2008, pp. 99-104, XP031284774.

Acar et al., "Safety Anterior Commissure-Posterior Commissure-Based Target Calculation of the Subthalamic Nucleus in Functional Stereotactic Procedures", Stereotactic Funct. Neurosura., 85:287-291, Aug. 2007.

Andrade-Souza, "Comparison of Three Methods of Targeting the Subthalamic Nucleus for Chronic Stimulation in Parkinson's Disease", Neurosurgery, 56:360-368, Apr. 2005.

Anheim et al., "Improvement in Parkinson Disease by Subthalamic Nucleus Stimulation Based on Electrode Placement", Arch Neural., 65:612-616, May 2008.

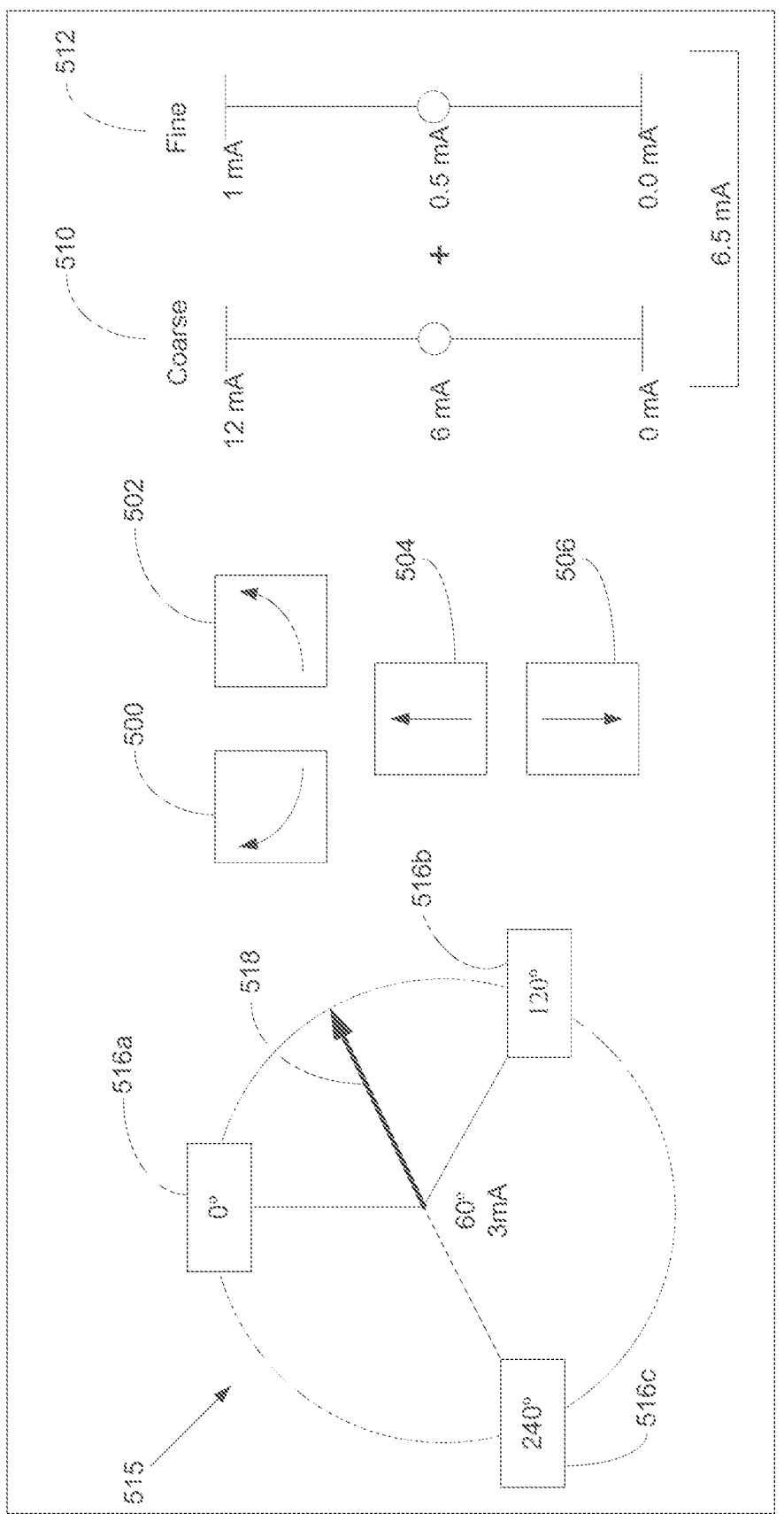

POINT-AND-CLICK PROGRAMMING FOR DEEP BRAIN STIMULATION USING REAL-TIME MONOPOLAR REVIEW TRENDLINES

CROSS-REFERENCE TO RELATED APPLICATIONS

The present application is a continuation of U.S. patent application Ser. No. 18/118,660, filed Mar. 7, 2023, which is a continuation of U.S. patent application Ser. No. 17/170,677, filed Feb. 8, 2021, which is a continuation of U.S. patent application Ser. No. 16/284,917, filed Feb. 25, 2019, which issued as U.S. Pat. No. 10,946,201, which is a continuation of U.S. patent application Ser. No. 15/991,807 filed May 29, 2018, which issued as U.S. Pat. No. 10,265,532, which is a continuation of U.S. patent application Ser. No. 15/729,383 filed Oct. 10, 2017, which issued as U.S. Pat. No. 10,016,610 on Jul. 10, 2018, which is a continuation of U.S. patent application Ser. No. 15/420,842 filed Jan. 31, 2017, which issued as U.S. Pat. No. 9,821,167 on Nov. 21, 2017, which is a divisional of U.S. patent application Ser. No. 15/012,698 filed Feb. 1, 2016, which issued as U.S. Pat. No. 9,561,380 on Feb. 7, 2017, which is a divisional of U.S. patent application Ser. No. 14/011,817 filed Aug. 28, 2013, which issued as U.S. Pat. No. 9,248,296 on Feb. 2, 2016, which claims priority to U.S. Provisional Patent Application Ser Nos. 61/693,866 filed on Aug. 28, 2012, 61/699,135 filed on Sep. 10, 2012, 61/699,115 filed on Sep. 10, 2012, and 61/753,232 filed on Jan. 16, 2013, the content of all of which is hereby incorporated by reference herein in their entireties.

FIELD OF THE INVENTION

The present invention relates to a system and method for providing a user interface in which a representation of stimulation parameters of an electrode leadwire, for example that provides electrical stimulation to an anatomical region, e.g., a leadwire of a Deep Brain Stimulation (DBS) device or a Spinal Cord Stimulation (SCS) device, is provided. The present invention further relates additionally or alternatively to a system and method, using software which provides a visual point-and-click interface that allows a user to optimize a subject's (e.g., patient's) stimulation parameters, without the user having to keep track of the precise settings for each electrode.

BACKGROUND

Stimulation of anatomical regions of a patient is a clinical technique for the treatment of disorders. Such stimulation can include deep brain stimulation (DBS), spinal cord stimulation (SCS), Occipital NS therapy, Trigemenal NS therapy, peripheral field stimulation therapy, sacral root stimulation therapy, or other such therapies. For example, DBS may include stimulation of the thalamus or basal ganglia and may be used to treat disorders such as essential tremor, Parkinson's disease (PD), and other physiological disorders. DBS may also be useful for traumatic brain injury and stroke. Pilot studies have also begun to examine the utility of DBS for treating dystonia, epilepsy, and obsessive-compulsive disorder.

However, understanding of the therapeutic mechanisms of action remains elusive. The stimulation parameters, electrode geometries, or electrode locations that are best suited for existing or future uses of DBS also are unclear.

For conducting a therapeutic stimulation, a neurosurgeon can select a target region within the patient anatomy, e.g., within the brain for DBS, an entry point, e.g., on the patient's skull, and a desired trajectory between the entry point and the target region. The entry point and trajectory are typically carefully selected to avoid intersecting or otherwise damaging certain nearby critical structures or vasculature. A stimulation electrode leadwire used to provide the stimulation to the relevant anatomical region is inserted along the trajectory from the entry point toward the target region. The stimulation electrode leadwire typically includes multiple closely-spaced electrically independent stimulation electrode contacts.

The target anatomical region can include tissue that exhibit high electrical conductivity. For a given stimulation parameter setting, a respective subset of the fibers are responsively activated. A stimulation parameter can include a current amplitude or voltage amplitude, which may be the same for all of the electrodes of the leadwire, or which may vary between different electrodes of the leadwire. The applied amplitude setting results in a corresponding current in the surrounding fibers, and therefore a corresponding voltage distribution in the surrounding tissue. The complexity of the inhomogeneous and anisotropic fibers makes it difficult to predict the particular volume of tissue influenced by the applied stimulation. A treating physician typically would like to tailor the stimulation parameters (such as which one or more of the stimulating electrode contacts to use, the stimulation pulse amplitude, e.g., current or voltage depending on the stimulator being used, the stimulation pulse width, and/or the stimulation frequency) for a particular patient to improve the effectiveness of the therapy. Parameter selections for the stimulation can be achieved via tedious and variable trial-and-error, without visual aids of the electrode location in the tissue medium or computational models of the volume of tissue influenced by the stimulation. Such a method of parameter selection is difficult and time-consuming and, therefore, expensive. Moreover, it may not necessarily result in the best possible therapy.

Systems have been proposed that provide an interface that facilitates parameter selections. See, for example, U.S. patent application Ser. No. 12/454,330, filed May 15, 2009 ("the '330 application"), U.S. patent application Ser. No. 12/454,312, filed May 15, 2009 ("the '312 application"), U.S. patent application Ser. No. 12/454,340, filed May 15, 2009 ("the '340 application"), U.S. patent application Ser. No. 12/454,343, filed May 15, 2009 ("the '343 application"), and U.S. patent application Ser. No. 12/454,314, filed May 15, 2009 ("the '314 application"), the content of each of which is hereby incorporated herein by reference in its entirety.

Such systems display a graphical representation of an area within which it is estimated that there is tissue activation or volume of activation (VOA) that results from input stimulation parameters. The VOA can be displayed relative to an image or model of a portion of the patient's anatomy. Generation of the VOA may be based on a model of fibers, e.g., axons, and a voltage distribution about the leadwire and on detailed processing thereof. Performing such processing to provide a VOA preview in real-time response to a clinician's input of parameters is not practical because of the significant required processing time. Therefore, conventional systems pre-process various stimulation parameter settings to determine which axons are activated by the respective settings.

Those systems also provide interfaces via which to input selections of the stimulation parameters and notes concerning therapeutic and/or side effects of stimulations associated with graphically represented VOAs.

The leadwire can include cylindrically symmetrical electrodes, which, when operational, produce approximately the same electric values in all positions at a same distance from the electrode in any plain that cuts through the electrode. Alternatively, the leadwire can include directional electrodes that produce different electrical values depending on the direction from the electrode. For example, the leadwire can include multiple separately controllable electrodes arranged cylindrically about the leadwire at each of a plurality of levels of the leadwire.

Each electrode may be set as an anode or cathode in a bipolar configuration or as a cathode, with, for example, the leadwire casing being used as ground, in a monopolar arrangement. When programming a leadwire for tissue stimulation, e.g., DBS, the clinical standard of care is often to perform a monopolar review (MPR) upon activation of the leadwire in order to determine the efficacy and side-effect thresholds for all electrodes on the leadwire, on an electrode by electrode basis. Monopolar review, rather than bipolar review, is performed because monopolar stimulation often requires a lower stimulation intensity than bipolar stimulation to achieve the same clinical benefit. The MPR can inform the selection of a first clinical program (parameters for stimulation) for treating a patient. For example, in a single current source, voltage-controlled DBS device, a time-consuming review is performed involving sequentially measuring efficacy and side-effect thresholds for all electrodes of a leadwire and recording these threshold values. Such a tedious review is described in Volkmann et al., Introduction to the Programming of Deep Brain Stimulators, *Movement Disorders* Vol. 17, Suppl. 3, pp. 5181-S187 (2002) ("Volkmann"). See, for example, FIG. 3 of Volkmann and the corresponding text, which describes gradually increasing amplitude separately for each of a plurality of electrodes, and recording the amplitude at which a minimum threshold of therapeutic efficacy is observed, and the maximum amplitude that does not exceed a permitted adverse side-effect threshold.

SUMMARY

According to example embodiments, a leadwire includes multiple electrodes, for each of which a respective independent current source is provided, by which current can be "steered" longitudinally and/or rotationally about the leadwire for localization of stimulation at points between electrodes (such a point hereinafter referred to as a "virtual electrode"). The electrical variation about a leadwire produced by virtual electrodes creates an added layer of complexity concerning stimulation parameters and their effects. Example embodiments of the present invention provide a visual point-and-click interface that includes a graphical representation of a stimulation parameter for virtual electrodes, via which to input settings therefor, and/or via which to obtain and/or output annotations concerning stimulation parameters thereof. According to example embodiments of the present invention, the interface includes controls for gradual directional steering of current about the leadwire, without the requirement for separately setting individual electrical amplitude settings of the individual electrodes, where the steering occurs between actual and virtual electrodes, the interface further providing for the system to receive input of efficacy and adverse side effect information. According to an example embodiment, the obtained input is recorded in association with the settings for which the input was provided, the system thereby generating longitudinal and/or rotational maps of efficacy and side effect information arranged about the leadwire according to the actual and/or virtual electrode positions with which the efficacy and side effect information are associated.

Thus, according to an example embodiment of the present invention, the system performs an iterative process, where each iteration corresponds to a single selected stimulation parameter value, e.g., amplitude, to which value a respective electric field corresponds. For each iteration, the electric field is shifted to various actual and/or virtual electrode locations about the leadwire, and for each of a plurality of the locations to which the respective field of the iteration has been shifted, clinical information regarding therapeutic effect and/or adverse side effect for a stimulation produced by the electric field is recorded. After completion of an iteration, the value of the parameter is changed for a new iteration, in which the shifting and information recording is repeated for the new value. The information obtained during a plurality of the iterations is then usable for construction of a graph on which basis optimal settings are selectable. Such settings include, in an example embodiment, a combination of respective values of the parameter for a selected subset of electrodes of the leadwire.

BRIEF DESCRIPTION OF THE DRAWINGS

In the drawings, which are not necessarily drawn to scale, like numerals may describe similar components in different views. The drawings illustrate generally, by way of example, but not by way of limitation, various embodiments discussed in the present document.

FIG. 5 illustrates user interface components, by user interaction with which a system is configured to receive input of stimulation parameters, according to an example embodiment of the present invention.

DETAILED DESCRIPTION

Figure 1:
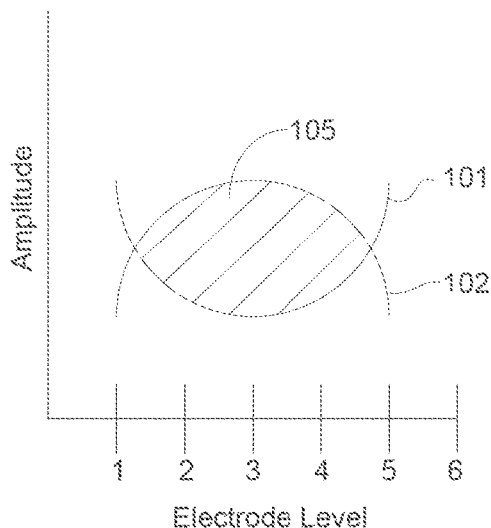
FIG. 1 shows graphs providing stimulation amplitude information for cylindrically symmetrical electrodes, according to an example embodiment of the present invention.

FIG. 1 shows an example graphical user interface display of output indicating amplitude information for stimulation using a cylindrically symmetric leadwire. With respect to a cylindrically symmetric leadwire, in an example embodiment, a graph is output in which stimulation amplitude values are plotted, for both a therapy onset curve 101 and side effect onset curve 102, against electrode location, where the electrode locations refer to longitudinal positions of the leadwire. For example, discrete positions along the abscissa can correspond to respective electrodes of the leadwire in their order of arrangement along the leadwire.

Alternatively, different combinations of amplitudes of the electrodes can be set, where each combination can be characterized as having an amplitude setting at a respective longitudinal position of the leadwire, producing a cylindrically symmetric stimulation about the leadwire at that respective longitudinal leadwire position. Positions along the abscissa can represent discrete locations from a first position of the leadwire towards another position of the leadwire, where some of the locations can be those of respective ones of the cylindrically symmetrical electrodes, and others can be other locations corresponding to the combination of stimulation settings of a plurality of the electrodes.

The therapy onset curve 101 indicates amplitude thresholds at which a therapeutic result is expected, depending on the electrode or longitudinal leadwire position at which the respective stimulation amplitude is set. The side effect onset curve 102 indicates a maximum stimulation amplitude at respective electrode or longitudinal leadwire positions, above which the stimulation is expected to cause an adverse side effect. Information on which the curves 101 and 102 are based can include empirically obtained data and/or model-based data. The graphs 101 and 102 can be specific to an indicated desired therapy and/or to an indicated adverse side effect. For example, the graphical user interface, e.g., in a target settings section, can include an input field for inputting a desired therapeutic effect and/or side effect to be avoided, and output a graph such that shown in FIG. 1 as information on which the user, e.g., a clinician, can determine settings to set in the system for producing a stimulation.

Such graphs can be useful for a clinician to eyeball a target range of possible target settings for one or more of the electrodes. For example, the clinician likely would choose to try an amplitude settings that falls at about the center of the shaded area 105 between the curves 101 and 102 since it is that region that is expected to produce a therapeutic effect and to avoid production of an adverse side effect.

However, such a representation does not reflect variations in amplitude at different directions cylindrically about the leadwire using directional electrodes. According to an example embodiment of the present invention, the system and method outputs stimulation amplitude information in a coordinate system in which each plotted data point is identified by a longitudinal position 'z', angle of rotation '0', and radius from center 'r', where the longitudinal position is the longitudinal position along the central axis of the leadwire, e.g., a distance from one of the ends, the angle of rotation is an angle between a selected direction extending outward from the leadwire, perpendicularly to the central axis thereof, and the direction in which stimulation is characterized as being produced by an electrode (or combination of electrodes), and radius is a distance from the leadwire along the direction in which the stimulation is characterized as being produced. The radius coordinate corresponds to the stimulation amplitude value, whereas the longitudinal position and angle of rotation information indicates the location of that stimulation. In an example embodiment of the present invention, a computer system provides a graphical user interface in which amplitude settings for a directional electrode leadwire are plotted in curves at planes that are perpendicular to the central axis of the leadwire according to the described coordinate system including longitudinal, angular, and radii values.

Figure 2:
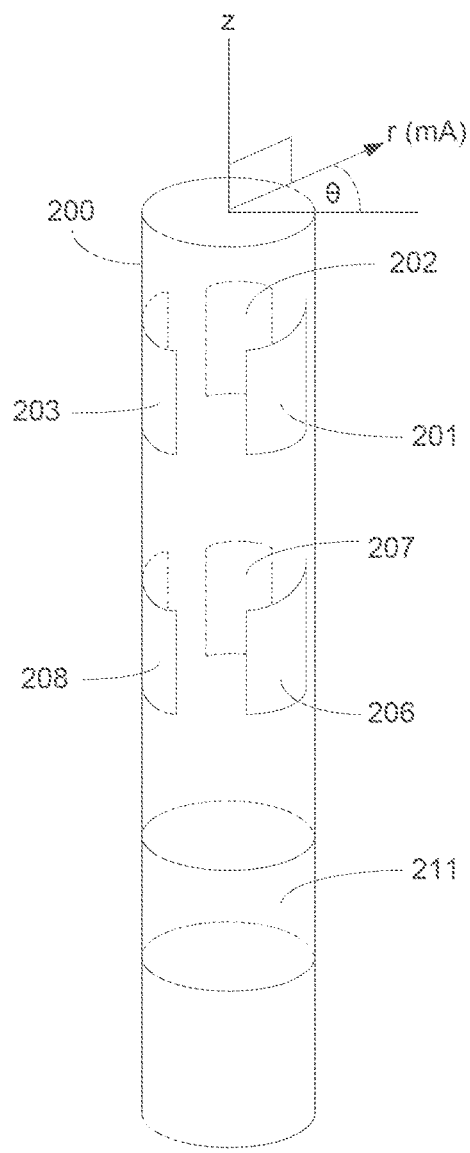
FIG. 2 shows an example leadwire model that is displayable by a system in a user interface, and further shows relative thereto a coordinate system for indicating amplitude information for directional electrodes, according to an example embodiment of the present invention.

FIG. 2 shows an example leadwire that includes a plurality of directional electrodes. In FIG. 2, the example leadwire 200 includes, at a first longitudinal level of the leadwire, three directional electrodes 201, 202, and 203, at a second longitudinal level of the leadwire, three directional electrodes 206, 207, and 208, and, at a third longitudinal level, a cylindrically symmetrical electrode 211 that is configured for generating a stimulation at approximately equal levels about the leadwire 200. While the directional electrodes are shown to be provided in groups about the leadwire, in an example embodiment, the leadwire 200 includes a circumferential directional electrode that continuously extends around the leadwire, but is controllable for generating stimulations at different levels in different directions from the leadwire.

FIG. 2 further shows a coordinate system in which amplitude values can be plotted using the 'z', '0', and 'r' coordinates. The coordinate system is shown relative to the illustrated leadwire 200, thereby showing the meaning of the coordinate values, which represent positional and amplitude information relative to the leadwire 200. Although the leadwire 211 is not a directional leadwire, the same coordinate system can be used for the cylindrically symmetrical leadwire too.

Figure 3:
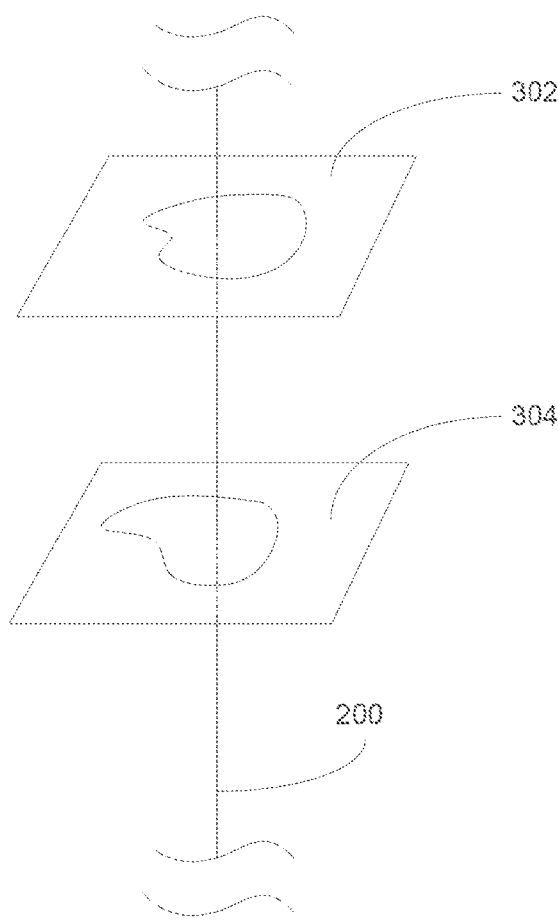
FIG. 3 shows amplitude information graphs for directional electrodes in a three-dimensional perspective, according to an example embodiment of the present invention.

FIG. 3 shows an example user interface display of graphed amplitude settings values using the described coordinate system for a directional leadwire. For example, a graph 302 and/or 304 is drawn with a perspective of being in a two dimensional plane perpendicular to the leadwire 200. Each of the illustrated graphs includes a shape formed by plotted values, for example, representing therapeutic threshold minimum values, i.e., values estimated as the minimum required amplitude for stimulation, where the estimated threshold minimum values vary depending on direction from the leadwire 200 at the longitudinal position of the leadwire 200 at which the plane is drawn. The graphs can alternatively represent maximum amplitude values above which a side effect is estimated to occur. As described below, graphs showing a combination of this information can also be provided.

Stimulation using a combination of electrodes at an one longitudinal level can produce stimulation values characterized by a stimulation at a direction which can be between the electrodes. Similarly, stimulation using a combination of electrodes at a plurality of longitudinal levels can produce stimulation values characterized by a stimulation at a level between electrodes above and below. Therefore, the displayed graphs need not be a longitudinal positions at which there are electrodes (although an alternative example embodiment can be provided in which the graphs are displayed only at longitudinal positions at which at least one electrode is located). In an example embodiment, using graphs plotting stimulations values characterized as occurring between electrodes by combinations of stimulations of those electrodes, the system plots a plurality of two dimensional graphs of stimulation values in a plurality of continuous layers to form a three dimensional graph volume.

In an example embodiment of the present invention, the system displays a model of the leadwire 200, e.g., as shown in FIG. 2 and further displays one or more graphs as shown in FIG. 3. The graphs can be displayed in a separate display area as that in which the model of the leadwire 200 is displayed, or can be displayed overlaid on the model of the leadwire 200. In an example embodiment of the present invention, the system and method of the present invention provides a graphical user interface including view rotation controls, by which a user can rotate the displayed model of the leadwire 200 and the displayed graphs.

Figure 4A:
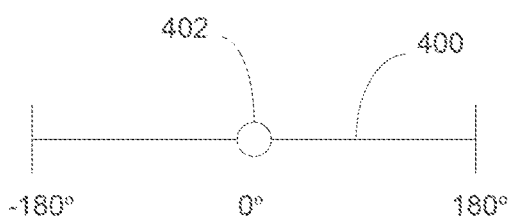
FIG. 4A shows a slider control for rotating a leadwire model, according to an example embodiment of the present invention.

For example, FIG. 4A shows a slide bar 400, with the center set at 0°, the right end at +180°, and the left end at −180°. A particular longitudinal line at a predetermined point along the circumference of the leadwire is selected as corresponding to 0°. The user can shift a slider control 402 along the slider bar 400, in response to which the system correspondingly rotates the model of the leadwire 200 (and the associated graphs). For example, in an example embodiment, the system shifts the model of the leadwire 200 so that that the selected angular portion of the leadwire 200 is positioned parallel with the surface of the screen in which the user interface is displayed.

Figure 4B:
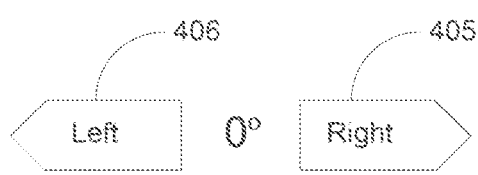
FIG. 4B shows left and right buttons for rotating a leadwire model, according to an example embodiment of the present invention.

Alternatively (or additionally), as shown in FIG. 4B, a right button 405 and a left button 406 can be displayed, which buttons are selectable using an input device, e.g., via point and click, touch, or any other suitably appropriate selection device/method, in response to which selection the model of the leadwire 200 is rotated towards the right or towards the left by a predetermined number of degrees per selection. In an example embodiment, the system displays an indication of the number of degrees the model of the leadwire 200 has been rotated, for example, as shown in FIG. 4B, between the selectable right and left buttons 405/406.

Figure 4C:
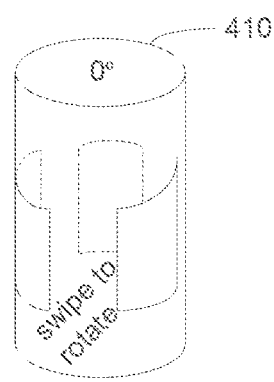
FIG. 4C shows a draggable interface component for rotating a leadwire model, according to an example embodiment of the present invention.

Alternatively (or additionally), as shown in FIG. 4C, the model of the leadwire 200 or a separate leadwire rotation control 410 that is selectable by the user and draggable to the right or to the left is displayed, where, in response to the dragging of the leadwire model 200 or the separate rotation control 410, the system correspondingly rotates the model of the leadwire 200 and the graphs. In an example embodiment, as shown in FIG. 4C, the system displays an indication of the number of degrees the model of the leadwire 200 has been rotated, for example, as shown in FIG. 4C, in a top cross-section of the leadwire representation of the leadwire rotation control 410.

In an example embodiment of the present invention, representations of respective electrodes in the model of the leadwire 200 or in the leadwire rotation control 410 are selectable, in response to which input, the system is configured to obtain user input of one or more settings to be set for the selected electrode. In an example embodiment, the system is configured to display one or more data fields in which to input parameter values for the selected electrode.

Figure 4D:
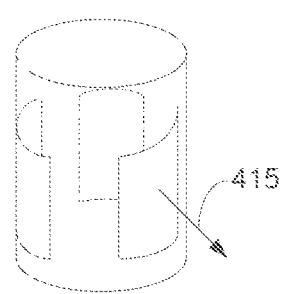
FIG. 4D shows a user interface control including a ray that is user-draggable rotationally about a point of origin corresponding to a leadwire and inward and outward with respect to the point of origin, for user modification of electrical parameters, according to an example embodiment of the present invention.

In an example embodiment, as shown in FIG. 4D, the system is configured to display a ray 415 extending from the selected electrode, which ray 415 the user can select and drag in a direction away from the representation of the leadwire 200 or towards the representation of the leadwire 200, where the system interprets dragging in the direction away from the representation of the leadwire 200 as an input to increase the amplitude setting, and the system interprets dragging back toward the representation of the leadwire 200 as an input to decrease the amplitude. The input can be by a clinician and, in an example embodiment, the system is configured to receive an instruction in response to which the system is configured to apply the modified setting to an implanted pulse generator that causes the leadwire 200 to produce the stimulation. Alternatively or additionally, the user-modification of the settings is for input of stimulation programs for which the system outputs information, e.g., a VOA, and/or other information, based on which the user can select a program to apply to the implanted pulse generator.

In an example embodiment of the present invention, the user interface display including the model of the leadwire 200 further includes a ray, like described ray 415, that extends from the model of the leadwire 200, and the ray is selectable and draggable towards the right and towards the left to modify a directionality of a stimulation, and inwards and outwards with respect to the model of the leadwire 200 to modify an amplitude of the stimulation in the selected direction.

FIG. 5 shows a part of a graphical user interface, according to an example embodiment, that can be displayed in a display device and that includes controls selectable by a user for input of stimulation settings, including a directionality, amplitude, and longitudinal locations relative to the leadwire, for a stimulation. The user interface includes a rotate left button 500, for modifying by the system of the directionality of a stimulation by clockwise rotation about the leadwire by a predetermined incremental amount, responsive to each selection thereof.

The user interface further includes a rotate right button 502, for modifying by the system of the directionality of the stimulation by counter-clockwise rotation about the leadwire by a predetermined incremental amount, responsive to each selection thereof. The user interface further includes one or more slider bars by which to modify the amplitude of the stimulation. For example, as shown in FIG. 5, in an example embodiment the user interface includes a coarse slider bar 510 in response to sliding of the slider control of which, the system modifies the amplitude by a first predetermined amount, e.g., a single digit whole number, for each change in position of the slider control; and also includes a fine slider bar 512 in response to sliding of the slider control of which, the system modifies the amplitude by a second predetermined amount smaller than the first predetermined amount, for fine increments between the selected coarse value set by the position of the coarse slider bar 510 and the next higher coarse value corresponding to the position of the coarse slider bar 510 that follows the current position thereof. For example, the coarse slider bar 510 can be set to be shifted between positions 0 and 12, a single whole number at a time, and the fine slider bar 512 can be set to be shifted between positions 0.0 and 0.9, a tenth at a time, so that for whichever value is set by the coarse slider bar 510, the value is further settable to an additional fractional amount.

The user interface further includes an up button 504 and a down button 506, for selection by the user of the longitudinal location along the leadwire at which the stimulation is to occur.

In an example embodiment, as shown in FIG. 5, the user interface further includes a, e.g., two dimensional, settings map 515 that shows present values of the settings with respect to directionality and amplitude of the stimulation. The settings map 515 includes a respective representations 516a-516c of each electrode at a particular longitudinal level. The settings map 515 includes a bar 518 angularly positioned according to the directionality of the stimulations according to the present settings, and whose length corresponds to the presently set amplitude of the stimulation. As the user provides input, e.g., via controls 500, 502, 510, and 512, to modify the directionality and/or amplitude, the bar 518 is rotated and/or shortened or lengthened. In an example embodiment, as shown in FIG. 5, the present angle and amplitude are displayed in the settings map 515.

In an example embodiment of the present invention, the user interface shown in FIG. 5, described above, instead of providing for longitudinally steering the electrical, e.g., current, using the up and down buttons 504 and 506, the system provides for receiving respective input for each longitudinal level of electrodes, each respective input indicating a respective direction and amplitude, e.g., by use of the controls 500, 502, 510, and/or 512, and/or other input controls, e.g., as described herein. For example, for the leadwire 200 as shown in FIG. 2, which includes electrodes 201-203 at a first level, electrodes 206-208 at a second level, and electrode 211 at a third level, the system outputs three user interface sections, e.g., like that shown in FIG. 5, for separately inputting the directional and amplitude settings of the stimulation.

According to a variant of this embodiment, the buttons 504 and 506 are omitted since current steering is not supported. Alternatively, buttons 504 and 506 are provided, but, according to this embodiment, their selections do not cause the above-described current steering, but rather are used for traversing between settings of different electrode levels of the leadwire. For example, the user can use the controls shown in FIG. 5 (or other controls) to set the direction and amplitude for electrodes at a first longitudinal level of the leadwire, and then select one of buttons 504 and 506 to set the settings for the electrodes of, respectively, the next higher or lower longitudinal level of the leadwire.

In an example embodiment of the present invention, the stimulation controls and the settings map 515 are displayed in an interface in which a three-dimensional perspective of a model of the leadwire 200, e.g., as shown in FIG. 2, is also displayed, which model is rotatable, for example, as discussed above with respect to any of FIGS. 4A-4C, and the rotational orientation of the settings map 515 is set by the system to correspond to the rotational orientation of the three-dimensional perspective of the model of the leadwire 200, such that the settings map 515 is rotated when the three-dimensional perspective of the model is rotated.

Figure 6:
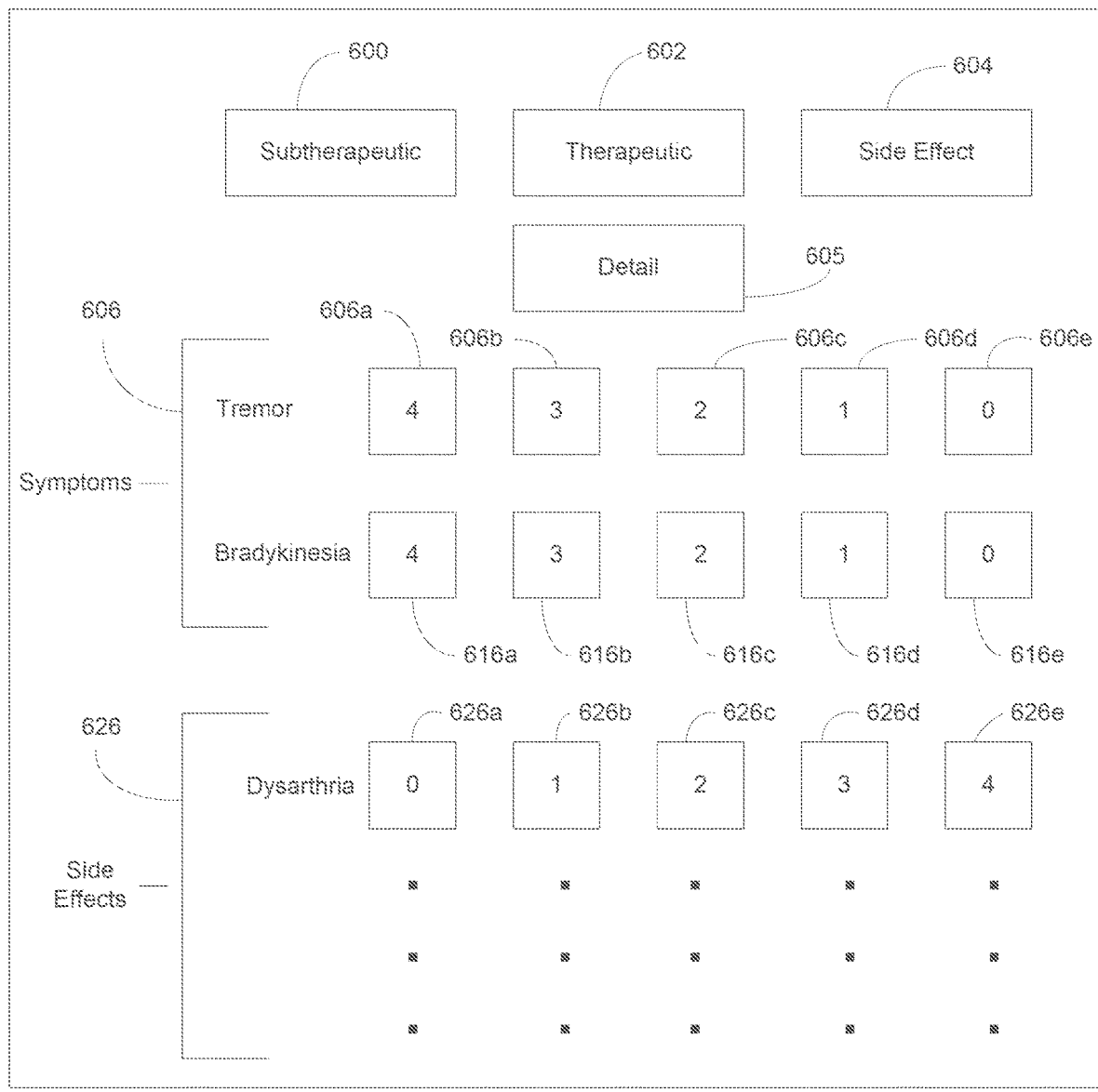
FIG. 6 illustrates user interface components, by user interaction with which a system is configured to receive input of annotations regarding stimulation settings, according to an example embodiment of the present invention.

As described above with respect to FIG. 3, according to example embodiments of the present invention, the system displays one or more graphs providing certain threshold (e.g., minimums and/or maximums) information using longitudinal, angular, and radii coordinates, regarding stimulation at various directions about the leadwire. In an example embodiment of the present invention, the system includes an interactive user interface with which a user can interact to input information usable by a processor to generate graphs such as those described with respect to FIG. 3. For example, FIG. 6 shows an example annotation control interface including annotation controls selectable by a user for inputting information concerning presently indicated settings. For example, in an example embodiment, the annotation control interface includes a sub-therapeutic button 600, which, if selected by the user, causes a processor of the system to record in memory information indicating that a stimulation at the presently indicated settings fail to produce a sufficiently therapeutic effect. In an example embodiment, the annotation control interface additionally or alternatively includes a therapeutic button 602, which, if selected by the user, causes a processor of the system to record in memory information indicating that a stimulation at the presently indicated settings fail produce a sufficiently therapeutic effect. In an example embodiment, the annotation control interface additionally or alternatively includes an over limit button 604, which, if selected by the user, causes a processor of the system to record in memory information indicating that a stimulation at the presently indicated settings produces an adverse side effect.

A therapy can cause both a therapeutic effect and an adverse side effect. Therefore, according to an example embodiment of the present invention, the system allows for input indicating both the therapeutic effect and the side effect.

According to an alternative example embodiment of the present invention, the annotation control interface includes a list of symptoms with an associated one or more input fields or selectable controls (e.g., discrete or by slider bar) by which to indicate a degree of therapeutic effect for that respective symptom and/or a list of adverse side effects with an associated one or more input fields or selectable controls (e.g., discrete or by slider bar) by which to indicate a degree to which the respective side effect is caused by the stimulation at the presently indicated settings. For example, as shown in FIG. 6, a symptoms section 606 lists the example symptoms of "tremor" and "bradykinesia" alongside each of which is a respective series of buttons selectable for inputting a respective degree of therapeutic effect for the respective symptom. For example, FIG. 6 shows a set of 5 buttons 606a-606e for inputting respective degrees of therapeutic effect for the symptom of tremor, for example, where selection of button 606a indicates a highest therapeutic effect and selection of button 606e indicates a lowest therapeutic effect (buttons 606b-606d indicating intermediate and progressively decreasing therapeutic effect). FIG. 6 similarly shows a set of 5 buttons 616a-616e similarly operable for the symptom of bradykinesia. FIG. 6 similarly shows a side effect section 626 which lists the example adverse side effect of "dysarthia" alongside which is a respective set of 5 buttons 626a-626e for inputting respective degrees of the adverse side effect of dysarthria, for example, where selection of button 626a indicates a lowest amount of side effect and selection of button 626e indicates a highest amount of side effect (buttons 626b-626d indicating intermediate and progressively increasing side effect).

In an example embodiment of the present invention, the controls for inputting specific therapeutic and side effect information, including identification of particular symptoms for which therapeutic effect is provided and/or identification of particular adverse side effects produced by the therapy, such as controls of sections 606 and 626, and the controls for inputting the more generalized information as to whether a therapeutic effect has been provided and/or a side effect has been produced, such as controls 600-604 are all provided by the system. For example, in an example embodiment of the present invention, the system initially displays controls 600-604, and, responsive to selection of a "details" button or tab 605, the system displays the controls for inputting the information in detailed form. For example, the system updates the interface to simultaneously display all of the controls 600-604 and 606a-626e. Alternatively, the system responsively replaces the generalized controls with the more specific controls. According to either embodiment, the system, in an example embodiment, toggles between the two types of displays responsive to repeated selection of the details button 605.

According to an example embodiment of the present invention, the system is configured to output different graphs as described with respect to FIG. 3 depending on user selectable filter criteria. For example, the user can filter for therapeutic effect related to tremor, in response to which filter the system is configured to output graphs like those shown in FIG. 3 indicating direction-dependent minimum amplitude values for producing a therapeutic effect for tremor, or can similarly filter for therapeutic effect related to bradykinesia. In an example embodiment, without input of a filter criterion, the system outputs a graph based on, for example, minimum amplitude values for producing a therapeutic effect of any kind, i.e., not limited to any one type of selected therapeutic effect.

Similarly, in an example embodiment of the present invention, the user can filter by adverse side effect, e.g., by dysarthria, in response to which filter the system is configured to output graphs like those shown in FIG. 3 indicating direction-dependent maximum amplitude values above which the particular selected side effect is expected to occur. In an example embodiment, without input of a filter criterion, the system outputs a graph based on, for example, maximum amplitude values beyond which any side effect has been recorded to have occurred, i.e., not limited to any one type of selected side effect.

Similarly, instead of or in addition to filtering by type of therapeutic effect and/or side effect, the system provides for filtering based on degree. For example, referring to FIG. 6, the user can filter for only those therapeutic effects indicated by at least a strength of that represented by button 606c, etc. Another example filter criterion is time. For example, the user can filter for graph generation based on input provided in a user-selected time period.

According to an example embodiment, if information is entered indicating the occurrence of a therapeutic effect or side effect, without additional details, e.g., by operation of one or more of the buttons 600-604, without providing additional details concerning degree or type, the system uses such information for the generation of a graph unconstrained by the above-described input criterion of degree and/or type, but does not consider such information for graphs provided in response to a user request constrained by such input criteria.

In an example embodiment of the present invention, the system is configured to output a combination of discrete graphs corresponding to respective types and/or degree. For example, in a plane drawn at a particular longitudinal position of the leadwire, the system outputs one or more graphs corresponding to therapeutic effect for tremor (at one or more degrees of effect) and one or more graphs corresponding to therapeutic effect for bradykinesia (at one or more degrees of effect). The system outputs indicia that identify the effect (and/or degree thereof) to which the different graphs correspond. For example, different colors (and/or hue, saturation, and/or transparency) can be used to represent different effects, and/or different labels can be displayed, e.g., perpetually or when selected or when a pointer is moved over or in close proximity to the graph. The system can similarly generate a plane of overlapping graphs corresponding to different side effects (and/or side effect severities).

Figure 7:
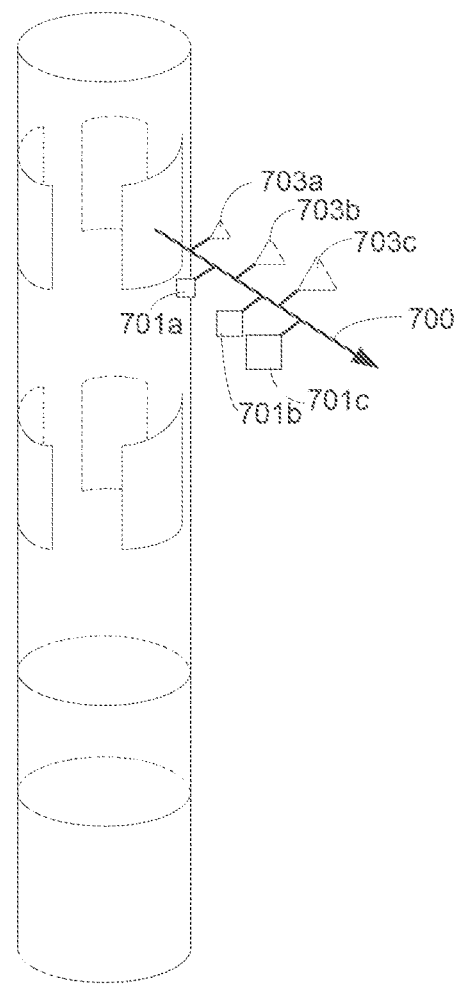
FIG. 7 illustrates user interface components for outputting variations in effect for variations in amplitude in a particular direction, according to an example embodiment of the present invention.

In an example embodiment of the present invention, instead of or in addition to a user interface display in which a plurality of graphs for different therapeutic effects, and/or side effects, and/or degrees thereof are included in a single plane, the graphs indicating directional dependency of the amplitude about the leadwire, the system is configured to indicate a variation of stimulation effect (e.g., adverse side effect or therapeutic effect) along a single selected direction from the leadwire as amplitude is increased. For example, FIG. 7 shows a user interface display including a model of a leadwire 200 with a ray 700 including markings at different locations of the ray corresponding to respective distances from the leadwire, which further corresponds to respective amplitude values. The markings can be provided at equal intervals. Alternatively, the markings can be provided wherever there is an appreciable change to the effect (e.g., where the system is programmed to indicate where a predefined difference value or percentage is reached). In an example embodiment, the markings indicate the degree of effect. For example a textual label or other indicia can be used. Further, in an example embodiment, a single ray is marked with different types of indicia for different types of information, e.g., different side effects or therapeutic effects. For example, ray 700 is marked by squares 701a-701c and triangles 703a-703c of different sizes, where squares 701a-701c indicate one type of effect, e.g., therapeutic effect for tremor, and triangles 703a-703c indicate another type of effect, e.g., therapeutic effect for bradykinesia, and where the sizes indicate the degree of such effect, e.g., small shapes indicating a slight effect and large shapes indicating a large effect.

While FIG. 7 shows a single ray 700 in a single direction, in an example embodiment, the system displays a plurality of such rays, each in a respective direction. For example, in an example embodiment, the system generates a display with a plurality of evenly spaced rays cylindrically about the leadwire. In an alternative example embodiment, the system is configured for receiving user input of one or more angles (i.e., directions), and the system accordingly displays respective rays for each of the input angles. In an example embodiment, the system, by default outputs a single ray for each directional electrode.

Figure 8:
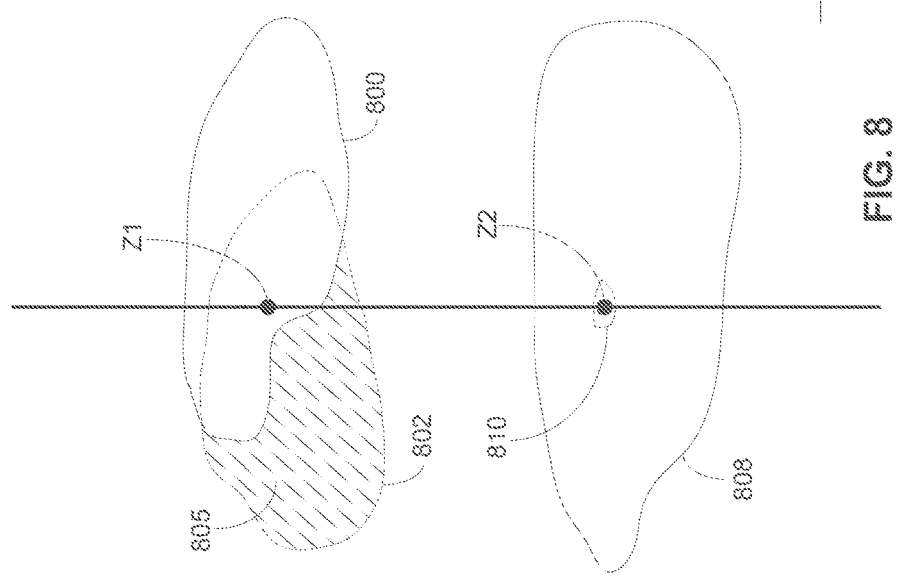
FIG. 8 illustrates a user interface display of information concerning suitable stimulation amplitude parameters for directional electrodes using graphs in a three-dimensional perspective, according to an example embodiment of the present invention.

As shown in FIG. 8, in an example embodiment of the present invention, the system is configured to output, in a single plane, graphs for both therapeutic effect and adverse side effect, which graphs can overlap depending on the respective minimum and maximum amplitude values of the graphs in the different directions about the leadwire. A user can thereby determine a range of amplitudes and an angular range about the leadwire at which to set the stimulation. In an example embodiment, the system is configured to mark a graph region determined to be suitable for stimulation based on the relationship between the area of the two graphs (where the graphs do indicate the existence of such a region).

For example, FIG. 8 shows a therapy onset graph 800 and a side effects graph 802 within a plane at longitudinal position z1. In an example embodiment, the system outputs indicia indicating which graph represents therapy onset values and which graph represents adverse side effects, each by line type or color and/or textual indicia, etc. It further includes a cross-hatched region 805, the cross-hatching indicating that region to represent suitable stimulation parameters. Any other suitably appropriate region indicia can be used, e.g., highlighting, coloring, or textual indicia, etc. The cross-hatched region is determined to represent suitable parameters because the parameters corresponding to that region are indicated to produce a therapeutic effect without producing an adverse side effect.

FIG. 8 further shows a therapy onset graph 808 and a side effects graph 810 within a plane at longitudinal position z2. No cross-hatched region is included because there is no suitable range of stimulation parameters at longitudinal position z2, since, in all directions about the leadwire, intolerable side effects set in at lower amplitudes than those at which therapeutic effects are first attained.

It is noted that that there may be certain adverse side effects that are tolerable and there may be certain therapeutic effects that are insignificant. The system is programmed to produce the graphical information for certain predetermined side effects and/or therapeutic effects. Additionally, in an example embodiment, the system includes a user interface via which a user can select one or more side effects and/or one or more therapeutic effects on which basis to generate the graphs.

Figure 9A:
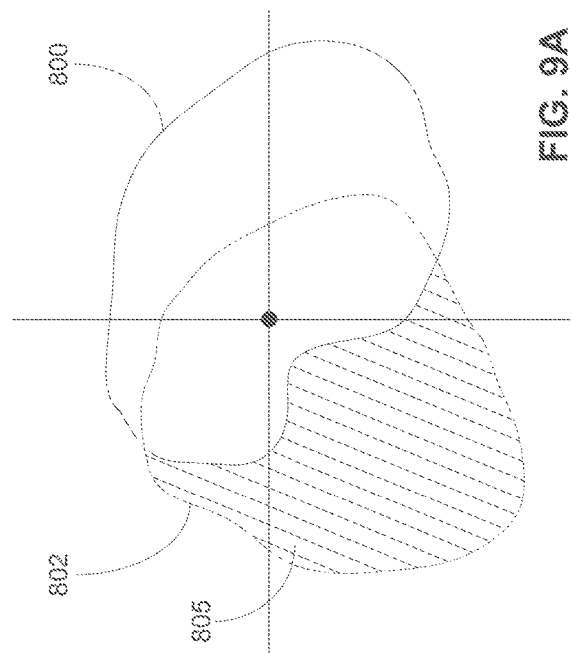
FIGS. 9A and 9B show user interface displays of the graphs of FIG. 8 in a two-dimensional perspective, according to an example embodiment of the present invention.
Figure 9B:
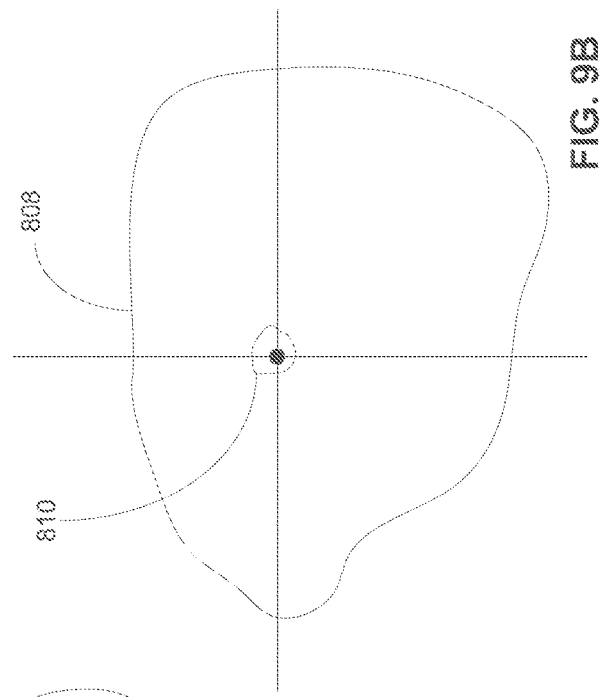

When the graphs are provided in a three-dimensional perspective about the model of the leadwire 200, the leadwire model can partially obscure portions of the graphs. Although, as discussed above, example embodiments provide a control for rotating the model, so that the graphs can be rotated and viewed at the different angles, a user may desire to view entire graphs at a time for the respective longitudinal positions at which they are generated. Additionally, when the graphs are provided in a three-dimensional perspective, precise dimensions of the graph shape are distorted to account for depth in a two-dimensional display screen, for example, as can be seen by a comparison of the graphs in FIG. 8 and their two-dimensional perspective counterparts shown in FIGS. 9A and 9B. Accordingly, in an example embodiment of the present invention, the system displays the graphs in a two dimensional view, in which the graphs of a single longitudinal position are displayed such that planes formed by the graphs are parallel to the surface of the display area, e.g., parallel to the surface of a display screen. For example, FIG. 9A shows the graphs 800 and 802 in a two-dimensional view with the leadwire virtually extending perpendicularly to the display screen, and FIG. 9B shows the graphs 808 and 810 in a two-dimensional view with the leadwire virtually extending perpendicularly to the display screen. In an example embodiment of the present invention, a two-dimensional view of graphs is displayed for only a single one of the longitudinal positions of the leadwire at any one time. Alternatively, in an example embodiment, different two-dimensional graph views for a plurality of longitudinal positions are simultaneously displayed in different respective display areas of the display screen, e.g., each area including respective indicia indicating the respective longitudinal position to which it corresponds.

Figure 10A:
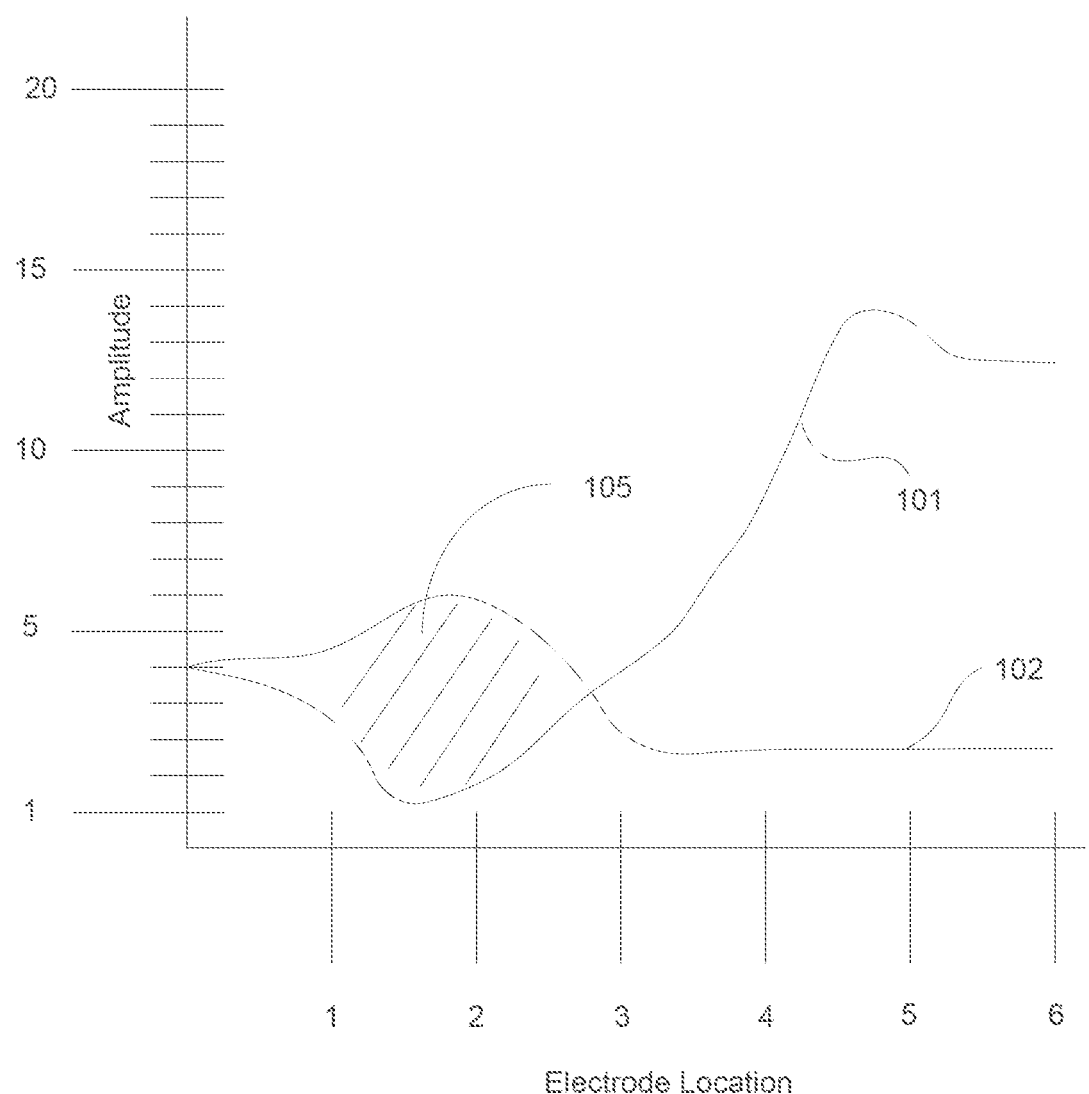
FIGS. 10A and 10B show graphs providing stimulation amplitude information for cylindrically symmetrical electrodes, according to an example embodiment of the present invention.
Figure 10B:
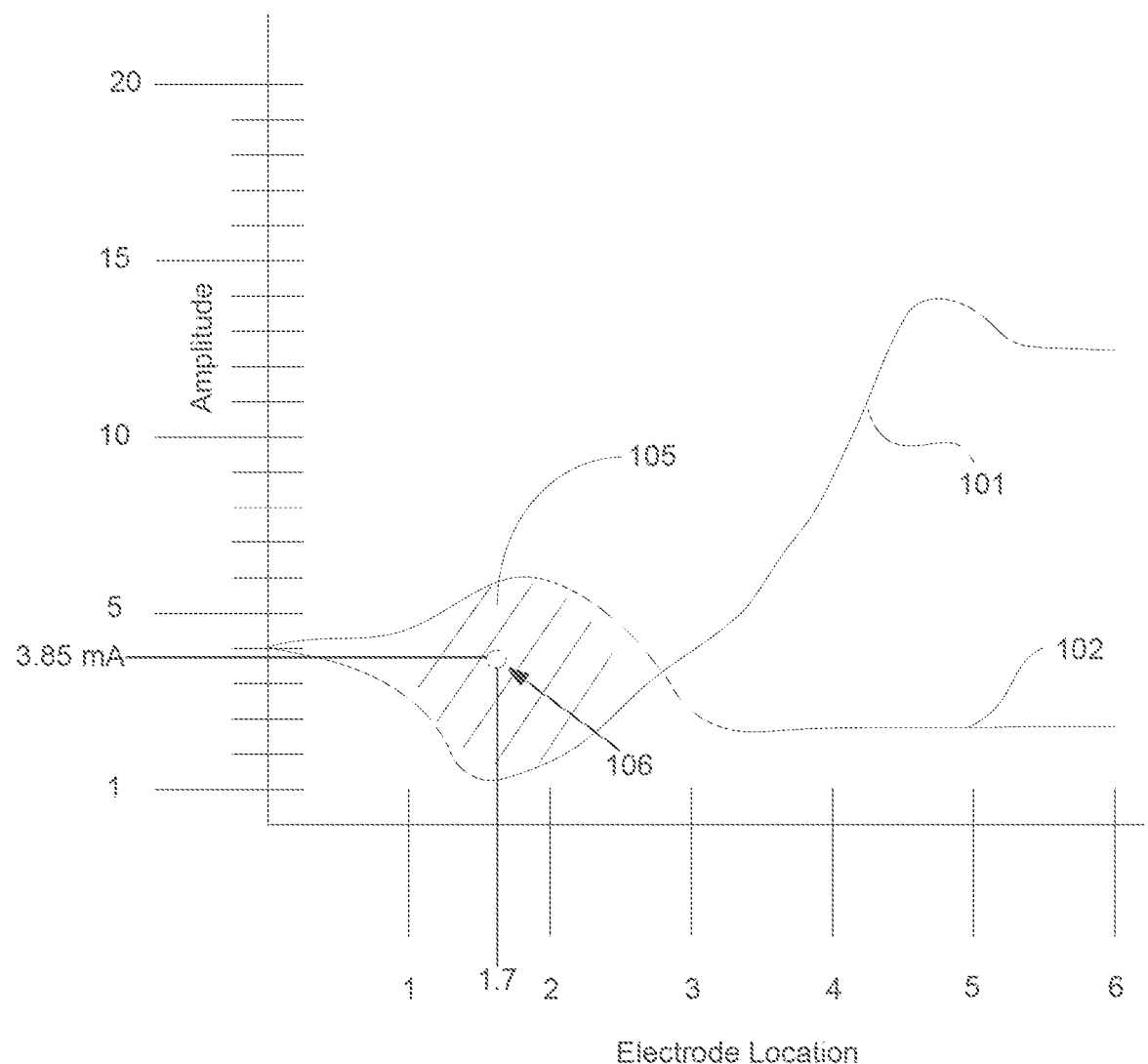

In an example embodiment of the present invention, the system displays a model of the leadwire 200, e.g., as shown in FIG. 2 and further displays one or more graphs as shown in FIGS. 10A and 10B (described below). The graphs can be displayed in a display area separate from that in which the model of the leadwire 200 is displayed, or can be displayed overlaid on the model of the leadwire 200. In an example embodiment of the present invention, the system and method of the present invention provides a graphical user interface including longitudinal steering controls and/or rotational steering controls, by which a user can, for a given fixed parameter (e.g., amplitude, pulse width, frequency, etc.), steer stimulation longitudinally up and down the electrodes of the leadwire and/or rotationally around the electrodes of the leadwire 200, including between actual and/or virtual electrodes, a process hereinafter referred to as e-trolling. At a plurality of arbitrary points (e.g., actual and/or virtual electrode) along the leadwire traversed via e-trolling, the efficacy and side-effects of a stimulation are evaluated. For example, if the patient exhibits undesireable side-effects, the user can annotate the stimulation at the actual or virtual electrode as being in a "side-effect range" by clicking on a button or menu item of the user interface, for example, using controls such as those shown in FIG. 6. Accordingly, if the patient exhibits good symptom relief or therapeutic efficacy, the user can annotate the current setting as being in an "efficacy range" by clicking on a button or menu item.

As explained above, FIG. 5 shows a part of a graphical user interface, according to an example embodiment, that can be displayed in a display device and that includes controls selectable by a user for input of stimulation settings, including a directionality, amplitude, and longitudinal locations relative to the leadwire, for a stimulation. The user interface includes a rotate left button 500, for modifying by the system of the directionality of a stimulation by clockwise rotation about the leadwire by a predetermined incremental amount, responsive to each selection thereof. The user interface further includes a rotate right button 502, for modifying by the system of the directionality of the stimulation by counter-clockwise rotation about the leadwire by a predetermined incremental amount, responsive to each selection thereof. The user interface further includes an up button 504 and a down button 506, for selection by the user of the longitudinal location along the leadwire at which the stimulation is to occur. In the case of a leadwire 200 with only non-directional, circumferential (cylindrically symmetrical) electrodes only an up button 504 and a down button 506, for selection by the user of the longitudinal location for stimulation along the leadwire, are provided or are active. (As noted above, the up and down buttons 504 and 506, according to an alternative example embodiment, provide for selecting a longitudinal level at which to set current information for the electrodes at that level.)

According to an example embodiment, information concerning therapeutic effect and/or adverse side effect is additionally or alternatively obtained using sensors. For example, a sensor can be used to sense patient tremor, speed, stability, heart rate, etc., based on which sensed information conclusions concerning therapeutic effect and/or side effect are automatically made and recorded.

Thus, according to an example embodiment of the present invention, a user interface facilitates gradual steering of a current, e.g., at a certain amplitude, frequency, and/or pulse width, about the leadwire, and user annotation of the steered current at various actual and/or virtual electrodes at which the current has been steered, as being in an "efficacy range" or a "side-effects range," by clicking a button or menu item for those electrode locations. According to an example embodiment, the determination of whether the steered current, at an actual and/or virtual electrode at which the current has been steered, is in an "efficacy range" or a "side-effects range" is performed by a processor based on information concerning therapeutic effect and/or adverse side effect additionally or alternatively obtained using sensors. According to an example embodiment, the system records the input (and/or sensor) information in association with the electrode locations to which they correspond, and, based on the recorded information regarding a respective plurality of actual and/or virtual electrodes traversed via e-trolling, generates a curve that connects the annotated values for each such respective identified and annotated actual and/or virtual electrode, thereby graphically identifying the totality of the results (for a given stimulation parameter setting) for a set of electrodes of the leadwire 200 as shown in FIG. 10A. The generated curve includes estimated data for connecting the discrete respective values corresponding to the respective identified and annotated actual and/or virtual electrodes. The set of electrodes can include several cylindrically symmetrical electrodes arranged longitudinally along the leadwire 200 and/or can include several directional electrodes arranged circumferentially around the leadwire 200 at a same longitudinal level on the leadwire 200.

Similar to that shown in FIG. 1, FIG. 10A shows an example graphical user interface display of output indicating amplitude information for stimulation using a leadwire with cylindrically symmetrical circumferential electrodes. The graph is based on the recorded information regarding a respective plurality of actual and/or virtual electrodes traversed via e-trolling and includes a therapy onset (efficacy) curve 101 and a side effect onset (side effect) curve 102 that plot stimulation amplitude values for therapy onset (e.g., meeting a minimum threshold) and side effect onset (e.g., meeting a minimum threshold), against actual and virtual electrode locations, corresponding to longitudinal positions along the leadwire. For example, discrete positions along the abscissa can correspond to respective electrodes and virtual electrodes of the leadwire in their order of arrangement along the leadwire.

According to an alternative example embodiment, a three dimensional graph is used to plot variations in another, e.g., electrical, settings in addition to amplitude. A non-exhaustive list of examples of such parameters include pulse width and frequency. For example, an 'x' axis can correspond to electrode location, a 'y' axis can correspond to amplitude, and a 'z' axis can correspond to the other parameter, so that, for example, different amplitude values are plotted for different values of the other parameter at a same electrode position.

As shown in FIG. 10A, in an example embodiment of the present invention, the system is configured to output, in a single graph, curves for both therapeutic effect (efficacy) and adverse side effect (side effect) measured at multiple actual and/or virtual electrodes of leadwire 200, which curves can intersect depending on the respective minimum and maximum amplitude values of the curves in the different locations about the leadwire. A user can thereby determine a range of amplitudes and locations about the leadwire at which to set the stimulation. In an example embodiment, the system is configured to graphically identify a graph region determined to be suitable for stimulation based on the relationship between the area of the two graphs (where the graphs do indicate the existence of such a region). For example, the processor identifies electrode locations for which associated minimum therapeutic effect amplitude values have been recorded which are lower than side effect amplitude values recorded for the respective electrode locations, identifies the graph area between those values at the respective plotted electrode locations, and displays graphical indicia at the identified graph area. A non-exhaustive list of examples of such indicia include coloring, shading, and/or hatching.

The efficacy curve 101 indicates amplitude thresholds at (or above) which a therapeutic result is expected, depending on the electrode or other longitudinal leadwire position (virtual electrode) at which the respective stimulation amplitude is set. The side effect curve 102 indicates a maximum stimulation amplitude at respective electrode or virtual electrode positions, above which the stimulation is expected to cause an adverse side effect (e.g., above a maximum threshold for such an adverse side effect). Information on which the curves 101 and 102 are based can include empirically obtained data and/or model-based data. The curves 101 and 102 can be specific to an indicated desired therapy and/or to an indicated adverse side effect. For example, the graphical user interface, e.g., in a target settings section, can include an input field for inputting a desired therapeutic effect and/or side effect to be avoided, and output a graph such that shown in FIGS. 10A and 10B as information on which basis the user, e.g., a clinician, can determine settings to set in the system for producing a stimulation. The user can then select the settings for the leadwire electrodes by clicking on the location on the graph that appears to provide the largest therapeutic width, i.e. the location where there is the highest probability of efficacy combined with the lowest probability of an undesired side-effect. According to an example embodiment, the determination of the location where there is the highest probability of efficacy combined with the lowest probability of an undesired side-effect is performed by a processor based on information from curves 101 and 102.

In an example embodiment of the present invention, the graphs are continuously updated as more data points are added via the above-described method of e-trolling. The curve begins as a simple straight line fit between the identified and annotated locations and as more data are added other curve-fitting techniques can be used to better match the recorded values. Curve fitting is the process of constructing a curve, e.g., by use of a mathematical function, which is a best fit to a series of data points, possibly subject to constraints. Curve fitting can involve, e.g., interpolation, where an exact fit to the data is required, or smoothing, in which a "smooth" function is constructed that approximately fits the data. Any suitably appropriate curve fitting function may be used. Accordingly, the output graph, in an example, embodiment, plots information for electrode locations for which therapeutic and/or side effect data has not been obtained, by "filling in" such information based on the information obtained for surrounding electrode locations.

According to an example embodiment, the graphs are also and/or alternatively continuously updated to plot different amplitude values for the therapeutic and or side effect curves for those locations for which input had been previously received, and for which the plotted values had previously reflected such previously obtained input, as more data are added for the previously identified and annotated location. For example, different results may be observed for settings for an electrode location at different times. Because of the variability in measured effects for a subject at a given stimulation location it is beneficial to overwrite any previous side effect threshold values for the location with a lower side effect threshold value for that location so that the user may be more sure about selecting stimulation parameters that will not cause undesired side effects. Likewise, it is beneficial to overwrite any previous efficacy threshold values for the location with a higher efficacy threshold value for that location so that the user may be more sure about selecting stimulation parameters that will produce therapeutic results, e.g. lessen undesired side effects. (Alternatively, averages can be plotted and/or the values to be plotted can be calculated based on a score affected by values of neighboring electrode locations.) Alternatively, time can be used as a third dimension, so that a user is able to see a history of the values.

The two-dimensional graph of FIG. 10A does not reflect variations in amplitude at different directions cylindrically about the leadwire 200 using directional electrodes. Therefore, according to an alternative example embodiment of the present invention, a two-dimensional graph is provided, where the positions along the abscissa represent locations from a first position of the leadwire 200 circumferentially towards another position on the leadwire 200, and where the locations are those of respective ones of actual directional electrodes (e.g., 201-203) and virtual directional electrodes arranged circumferentially on a same longitudinal level of the leadwire 200. In example embodiment, several such graphs are provided, each for a respective longitudinal level along the leadwire 200.

According to an alternative example embodiment, a two-dimensional graph is output, where positions along the abscissa represent longitudinal locations along the leadwire 200, as described above with respect to FIG. 10A, but where one or more of the represented longitudinal locations are respective longitudinal levels at which a plurality of directional electrodes are arranged, with the amplitude information for the therapeutic effect and side effect corresponding to respective combinations of the directional electrodes at the represented longitudinal locations. Others of the represented longitudinal locations can be those at which cylindrically symmetrical electrodes are located. The plotted amplitude levels for the levels at which directional electrodes are located are those generated by one or a combination of the directional electrodes at the respective longitudinal level. Accordingly, some information (i.e., directionality) is missing from the graph for the represented longitudinal levels at which directional electrodes are arranged. For example, in an example embodiment, one or more of the longitudinal positions correspond to those at which cylindrically symmetrical electrodes are located, so that directionality is not a factor, while one or more other longitudinal positions correspond to those at which directional electrodes are located, with directionality not being indicated.

According to an alternative example embodiment of the present invention, the system generates and outputs a three-dimensional graph, with amplitude plotted as radii, as shown in FIG. 3, with multiple layers of such graphs in combination providing a three-dimensional graph volume, as described above, in order to graphically indicate variations of the amplitude values for the therapeutic effect and side effect at different combinations of longitudinal and rotational electrode locations. That is, according to this embodiment, the therapeutic effect and adverse side effect information for the steered locations are plotted to show variations along both longitudinally steered locations and rotationally steered locations.

According to this embodiment, the system and method outputs stimulation amplitude information in a three dimensional coordinate system in which each plotted data point is identified by a longitudinal position 'z', angle of rotation 'θ', and radius from center 'r' as shown by the indicated coordinate system of FIG. 2. The longitudinal position is the longitudinal position along the central axis of the leadwire, e.g., a distance from one of the ends, the angle of rotation is an angle between a selected direction extending outward from the leadwire, perpendicularly to the central axis thereof, and the direction in which stimulation is characterized as being produced by an electrode (or combination of electrodes), and radius is a distance from the leadwire along the direction in which the stimulation is characterized as being produced. The radius coordinate corresponds to the stimulation amplitude value, whereas the longitudinal position and angle of rotation information indicates the location of that stimulation. In an example embodiment of the present invention, a computer system provides a graphical user interface in which amplitude settings for a directional electrode leadwire are plotted in curves at planes that are perpendicular to the central axis of the leadwire according to the described coordinate system including longitudinal, angular, and radii values.

In an example embodiment of the present invention, the system includes a control selectable for toggling between a three dimensional view of the graphs and two dimensional views of the graphs.

As noted above, there may be certain adverse side effects that are tolerable for a certain subject and there may be certain therapeutic effects that are insignificant for said subject. Therefore, in an example embodiment, the system includes a user interface via which a user can select one or more side effects and/or one or more therapeutic effects on which basis to generate the graphs.

Such graphs can be useful for a clinician to eyeball a target range of possible target stimulation settings for one or more of the electrodes. For example, with respect to the graph shown in FIG. 10A, the clinician likely would choose to try stimulation (amplitude+electrode location) settings that fall at about the center of the shaded area 105 between the curves 101 and 102 since it is that region that is expected to produce a therapeutic effect and to avoid production of an adverse side effect.

According to an example embodiment of the present invention, the graph is output as a user-interactive display, where positions within the graph are user-selectable as an instruction to set electrode parameters. For example, as shown in FIG. 10B, in an example embodiment of the present invention, the user interface is configured for the user to point and click on a location within the graph, the selected location being identified in FIG. 10B as location 106, which the user (or system) has determined is likely a location with a high side effect threshold and a large therapeutic width (low efficacy threshold). The system is configured to, responsive to the selection, automatically choose a combination of electrode location and amplitude (and/or other stimulation parameter) associated with the selected point 106 on the graph, for output of the identified parameters in a user interface and/or for setting of the leadwire 200 to produce a stimulation according to such parameters.

Figure 11:
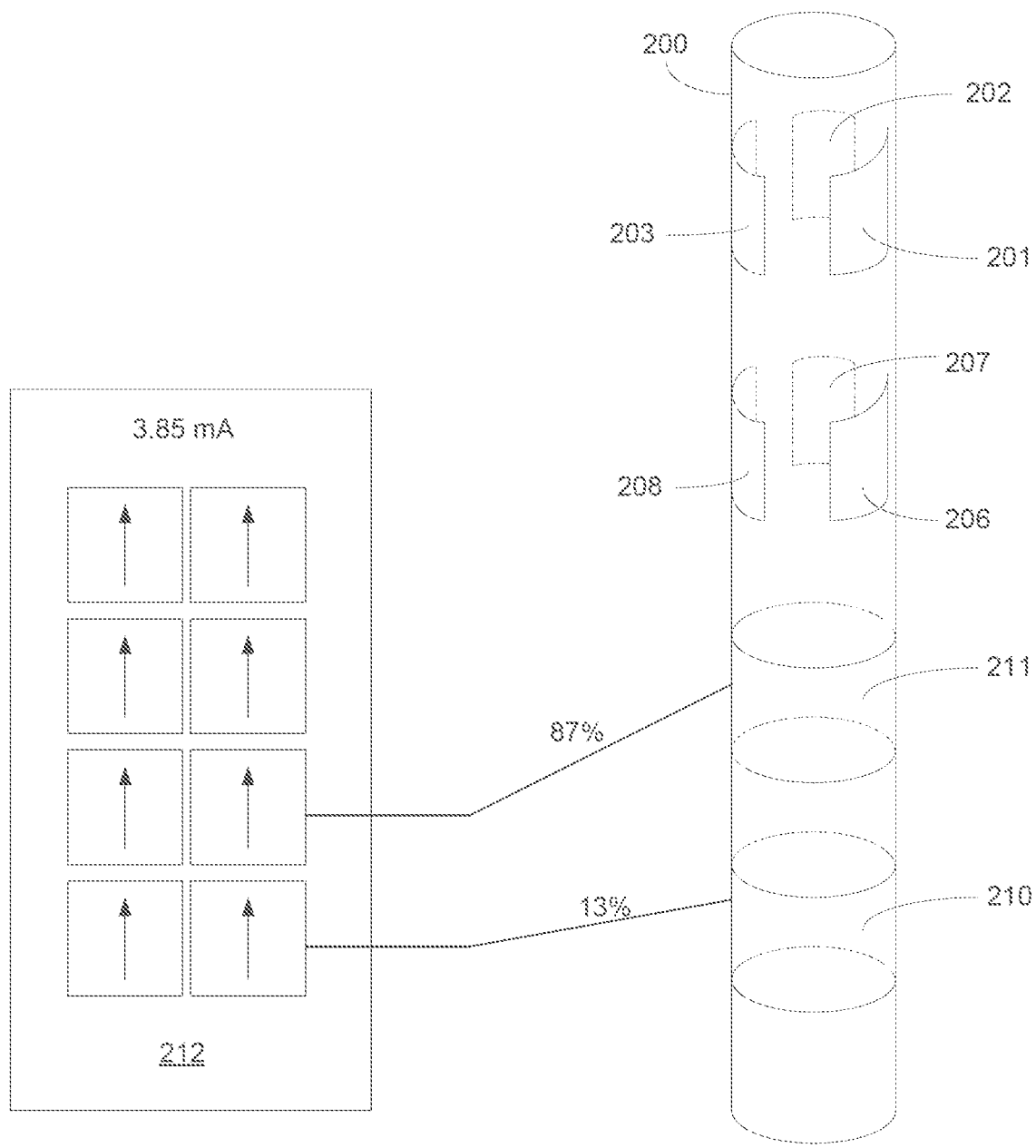
FIG. 11 shows an example leadwire model that is programmed by a system via a user interface, and further shows relative thereto, location and current level information for stimulation at a specified amplitude, according to an example embodiment of the present invention.

FIG. 11 shows a representation of a plurality of independently controllable current sources 212 for respective ones of the electrodes of the leadwire 200, where the current steering described above, for steering of the current to virtual electrode positions (longitudinally and/or rotationally), is possible by setting the amplitudes of different ones of the current sources 212 to different settings. For example, for settings corresponding to the selected location 106, the system is configured to choose the combination of electrode location and amplitude (and/or other stimulation parameter) associated with the selected point 106 on the graph as a combination of current amplitude values for a respective combination of the current sources 212. The independently controllable current sources 212 for the respective electrodes can be activated in accordance with the stimulation settings associated with selected point 106, e.g., for an amplitude of 3.85 mA and virtual electrode location 1.7, which is closer to the second electrode 211 of leadwire 200 than to the first electrode 210. The stimulation current settings required to localize the stimulation in the area of the virtual electrode associated with the selected point 106 are determined automatically by the system once the point 106 is selected by a user. In an example embodiment of the present invention, the system uses data previously recorded during the e-trolling, regarding the stimulation current settings required to localize the stimulation in the area of the virtual electrode associated with the selected point, if it is available for the selected point. In the example of FIG. 11, electrode 210 receives 13% of the max current and electrode 211 receives 87% of the max current so that the stimulation is localized at an electrode location corresponding to a virtual electrode located longitudinally between cylindrically symmetrical electrodes 210 and 211 and closer to electrode 211 than to electrode 210.

In an example embodiment of the present invention, a leadwire 200 utilizing a single current source for all of the electrodes of the leadwire 200 is used, and after the user has selected a point associated with stimulation parameters and clinical data on a graph provided according to the user interface described for virtual electrode steering, the system uses pulse interleaving to approximate the stimulation localized in an area of the corresponding virtual electrode. The pulse interleaving uses a single current source that alternates between different current settings at high speed for the different electrodes of the leadwire 200, to provide the different current amplitudes to different ones of the electrodes of leadwire 200 in an alternating manner. In this way, the separate electrodes (e.g., 210 and 211) can receive short-timed pulses from the same current source at different current values (e.g., 13% and 87%) so that stimulation is localized in an area of the corresponding virtual electrode.

As described in detail above, in an example embodiment of the present invention, for a set of stimulation parameters, the system outputs a graphical representation of the parameters in the form of a ray extending from a model of the leadwire, where the directionality and length of the ray represents, respectively, a directionality of the stimulation produced by the parameters and the electrical amplitude. In an example embodiment, the system additionally outputs information regarding tissue stimulation produced by the electrical stimulation parameters represented by the array. For example, in an example embodiment, the system displays a first user interface frame identifying one or more of the stimulation parameters and/or including a graphical representation thereof, e.g., in the form of the described graphical information, and further displays a second user interface section displaying an estimated VOA, e.g., as described in the '330, '312, '340, '343, and '314 applications, corresponding to the indicated and/or represented stimulation parameters.

An example embodiment of the present invention is directed to one or more processors, which can be implemented using any conventional processing circuit and device or combination thereof, e.g., a Central Processing Unit (CPU) of a Personal Computer (PC) or other workstation processor, to execute code provided, e.g., on a hardware computer-readable medium including any conventional memory device, to perform any of the methods described herein, alone or in combination, and to generate any of the user interface displays described herein, alone or in combination. The one or more processors can be embodied in a server or user terminal or combination thereof. The user terminal can be embodied, for example, as a desktop, laptop, hand-held device, Personal Digital Assistant (PDA), television set-top Internet appliance, mobile telephone, smart phone, etc., or as a combination of one or more thereof. Specifically, the terminal can be embodied as a clinician programmer terminal, e.g., as referred to in the '330, '312, '340, '343, and '314 applications. Additionally, as noted above, some of the described methods can be performed by a processor on one device or terminal and using a first memory, while other methods can be performed by a processor on another device and using, for example, a different memory.

The memory device can include any conventional permanent and/or temporary memory circuits or combination thereof, a non-exhaustive list of which includes Random Access Memory (RAM), Read Only Memory (ROM), Compact Disks (CD), Digital Versatile Disk (DVD), and magnetic tape.

An example embodiment of the present invention is directed to one or more hardware computer-readable media, e.g., as described above, having stored thereon instructions executable by a processor to perform the methods and/or provide the user interface features described herein.

An example embodiment of the present invention is directed to a method, e.g., of a hardware component or machine, of transmitting instructions executable by a processor to perform the methods and/or provide the user interface features described herein.

The above description is intended to be illustrative, and not restrictive. Those skilled in the art can appreciate from the foregoing description that the present invention can be implemented in a variety of forms, and that the various embodiments can be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and the following listed features.

What is claimed is:

1. A method for identifying clinical effects of electrical stimulation, the method comprising:
   providing a leadwire implanted in patient tissue and comprising a plurality of electrodes, wherein the plurality of electrodes comprises at least one set of two or more directional electrodes, wherein the directional electrodes of each of the at least one set are disposed at a same longitudinal level of the leadwire but at different circumferential positions;
   for each of a plurality of different combinations of values of a) a particular stimulation parameter and b) a directionality of the stimulation, stimulating the patient tissue using the values of the particular stimulation parameter and the directionality of the stimulation and obtaining a first clinical effect, selected from a plurality of different effects, produced thereby and a degree of the first clinical effect selected from a plurality of different degrees, the plurality of different degrees comprising at least a high degree of the first clinical effect and a low degree of the first clinical effect; and
   displaying a graph plotting the obtained first clinical effects as respective data points, wherein, for each of the data points, a color, hue, saturation, transparency, or size of the displayed data point indicates the degree of the obtained first clinical effect.

2. The method of claim 1, wherein the color, hue, saturation, transparency, or size of the displayed data point further indicates a type of the obtained first clinical effect.

3. The method of claim 2, wherein a one of the color, hue, saturation, transparency, shading, size, or hatching of the displayed data point indicates the degree of the obtained first clinical effect and a different one of the color, hue, saturation, transparency, or size of the displayed data point indicates the type of the obtained first clinical effect.

4. The method of claim 1, wherein the plurality of different degrees for the first clinical effect comprises at least three different degrees.

5. The method of claim 1, wherein the first clinical effect is a therapeutic effect.

6. The method of claim 1, wherein the first clinical effect is a side effect.

7. The method of claim 1, wherein the obtaining further comprises obtaining a degree of a second clinical effect selected from a plurality of different degrees.

8. The method of claim 1, wherein, for at least one of the different combinations of values of a) the particular stimulation parameter and b) the directionality of the stimulation, the obtaining further comprises obtaining a second clinical effect, selected from the plurality of different effects, produced by the stimulating and a degree of the second clinical effect selected from a plurality of different degrees.

9. A system for selecting electrical stimulation parameters, the system comprising:
a leadwire configured for implantation in patient tissue and comprising a plurality of electrodes, wherein the plurality of electrodes comprises at least one set of two or more directional electrodes, wherein the directional electrodes of each set are disposed at a same longitudinal level of the leadwire but at different circumferential positions;
an implantable pulse generator coupled to the leadwire and configured to stimulate the patient tissue using the leadwire;
a screen;
a processor coupled to the screen and configured execute instructions, the instructions, when executed, are configured to:
for each of a plurality of different combinations of values of a) a particular stimulation parameter and b) a directionality of the stimulation, direct stimulation of the patient tissue using the values of the particular stimulation parameter and the directionality of the stimulation and obtain a first clinical effect, selected from a plurality of different effects, produced thereby and a degree of the first clinical effect selected from a plurality of different degrees, the plurality of different degrees comprising at least a high degree of the first clinical effect and a low degree of the first clinical effect; and
display, on the screen, a graph plotting the obtained first clinical effects as respective data points, wherein, for each of the data points, a color, hue, saturation, transparency, or size of the displayed data point indicates the degree of the obtained first clinical effect.

10. The system of claim 9, wherein the color, hue, saturation, transparency, or size of the displayed data point further indicates a type of the obtained first clinical effect.

11. The system of claim 10, wherein a one of the color, hue, saturation, transparency, shading, size, or hatching of the displayed data point indicates the degree of the obtained first clinical effect and a different one of the color, hue, saturation, transparency, or size of the displayed data point indicates the type of the obtained first clinical effect.

12. The system of claim 9, wherein the plurality of different degrees for the first clinical effect comprises at least three different degrees.

13. The system of claim 9, wherein the first clinical effect is a therapeutic effect.

14. The system of claim 9, wherein the first clinical effect is a side effect.

15. The system of claim 9, wherein the obtaining further comprises obtaining a degree of a second clinical effect selected from a plurality of different degrees.

16. The system of claim 9, wherein, for at least one of the different combinations of values of a) the particular stimulation parameter and b) the directionality of the stimulation, the obtaining further comprises obtaining a second clinical effect, selected from the plurality of different effects, produced by the stimulating and a degree of the second clinical effect selected from a plurality of different degrees.

17. A non-transitory computer-readable medium having instructions stored thereon, the instructions, when executed by a processor, are configured to:
for each of a plurality of different combinations of values of a) a particular stimulation parameter and b) a directionality of stimulation, direct stimulation of patient tissue using the values of the particular stimulation parameter and the directionality of the stimulation and obtain a first clinical effect, selected from a plurality of different effects, produced thereby and a degree of the first clinical effect selected from a plurality of different degrees, the plurality of different degrees comprising at least a high degree of the first clinical effect and a low degree of the first clinical effect; and
direct display of a graph plotting the obtained first clinical effects as respective data points, wherein, for each of the data points, a color, hue, saturation, transparency, or size of the displayed data point indicates the degree of the obtained first clinical effect.

18. The non-transitory computer-readable medium of claim 17, wherein the color, hue, saturation, transparency, or size of the displayed data point further indicates a type of the obtained first clinical effect.

19. The non-transitory computer-readable medium of claim 18, wherein a one of the color, hue, saturation, transparency, shading, size, or hatching of the displayed data point indicates the degree of the obtained first clinical effect and a different one of the color, hue, saturation, transparency, or size of the displayed data point indicates the type of the obtained first clinical effect.

20. The non-transitory computer-readable medium of claim 17, wherein the plurality of different degrees for the first clinical effect comprises at least three different degrees.

* * * * *